(12) United States Patent
Jonckers et al.

(10) Patent No.: US 9,932,346 B2
(45) Date of Patent: Apr. 3, 2018

(54) PYRROLOPYRIMIDINES FOR USE IN INFLUENZA VIRUS INFECTION

(71) Applicant: Janssen Sciences Ireland UC, County Cork (IE)

(72) Inventors: Tim Hugo Maria Jonckers, Heist op den Berg (BE); David Craig McGowan, Brussels (BE); Pierre Jean-Marie Bernard Raboisson, Rosieres (BE); Werner Constant Johan Embrechts, Beerse (BE); Jérôme Émile Georges Guillemont, Andé (FR)

(73) Assignee: Janssen Sciences Ireland UC, Eastgate, Little Island, County Cork (IE)

( * ) Notice: Subject to any disclaimer, the term of this patent is extended or adjusted under 35 U.S.C. 154(b) by 0 days.

(21) Appl. No.: 15/509,474

(22) PCT Filed: Sep. 7, 2015

(86) PCT No.: PCT/EP2015/070316
§ 371 (c)(1),
(2) Date: Mar. 7, 2017

(87) PCT Pub. No.: WO2016/037953
PCT Pub. Date: Mar. 17, 2016

(65) Prior Publication Data
US 2017/0253600 A1    Sep. 7, 2017

(30) Foreign Application Priority Data

Sep. 8, 2014  (EP) .................................... 14183984

(51) Int. Cl.
*C07D 487/04*     (2006.01)
*A61K 31/519*     (2006.01)

(52) U.S. Cl.
CPC .......... *C07D 487/04* (2013.01); *A61K 31/519* (2013.01)

(58) Field of Classification Search
None
See application file for complete search history.

(56) References Cited

FOREIGN PATENT DOCUMENTS

| WO | WO 2007/041130 A1 | 4/2007 |
| WO | WO 2010/148197 A1 | 12/2010 |
| WO | WO 2012/083117 A1 | 6/2012 |
| WO | WO 2012/083122 A1 | 6/2012 |
| WO | WO 2013/019828 A1 | 2/2013 |

OTHER PUBLICATIONS

Chawla et. al. Current Research & Information on Pharmaceutical Science, 2004, 5(1), p. 9-12.*
Newman et. al.; Drug Discovery Today; 2003, 8(19) p. 898-905.*
Narayanan, et al, Expert Opinion on Investigational Drugs, 2011, vol. 20(2), pp. 239-254.
International Search Report and Written Opinion of PCT/EP2015/070316 dated Oct. 30, 2015.

* cited by examiner

*Primary Examiner* — Jeffrey H Murray

(57) ABSTRACT

The invention relates to compounds having the structure of formula (I) which can be used for the treatment of or against influenza infections.

19 Claims, No Drawings

PYRROLOPYRIMIDINES FOR USE IN INFLUENZA VIRUS INFECTION

CROSS-REFERENCE TO RELATED APPLICATIONS

This application is a national phase entry of International Application No. PCT/EP2015/070316, filed on Sep. 7, 2015, which claims priority to EP Patent Application No. 14183984.5, filed on Sep. 8, 2014, each of which is incorporated herein in its entirety.

Influenza is a serious public health problem with a high incidence in the human population resulting in regular large-scale morbidity and mortality. It is a highly contagious airborne disease that causes an acute febrile illness. Systemic symptoms vary in severity from mild fatigue to respiratory failure and death. According to the WHO the average global burden of annual epidemics may be on the order of 1 billion cases, 3-5 million cases of severe illness and 300,000-500,000 deaths annually. Every year, influenza viruses circulate in humans, typically affecting 5-20% of the population in all age groups, with this figure rising up to 30% during major epidemics. Rates of serious illness and death are highest among persons aged >65 years, children aged <2 years, and persons of any age who have medical conditions that place them at increased risk for complications from influenza, such as chronic heart, lung, kidney, liver, blood or metabolic diseases, or weakened immune systems. Although deaths are infrequent among children, rates of hospitalization range from approximately 100 to 500 per 100,000 for children <5 years-old, depending on the presence or absence of co-morbid conditions. Hospitalization rates among children aged <24 months are comparable to rates reported among persons aged >65 years.

In the US, annual influenza epidemics lead to approximately 30 million outpatient visits, resulting in medical costs of $10 billion annually. Lost earnings due to illness and loss of life represent a cost of over $15 billion annually and the total US economic burden of annual influenza epidemics amounts to over $85 billion.

Pathogens that cause influenza are negative sense, single-stranded RNA viruses, which belong to the family of Orthomyxoviridae. There are three types of influenza viruses: A, B and C. Influenza A viruses are the most common form, which can spread in mammals and birds. The subtypes of influenza A are named by the types of surface proteins hemagglutinin (H) and neuraminidase (N). There are 18 different hemagglutinin and 11 known neuraminidases. Current seasonal influenza viruses found in human are mainly H1N1 and H3N2 subtypes. Influenza B viruses are usually found only in humans. They are not divided into subtypes, but can be further broken down into different strains. Circulating influenza viruses are highly variable each year, and both influenza A and B cause seasonal epidemics all over the world. Influenza C viruses give much milder symptoms, which do not cause epidemics.

All three types of viruses have similar genome structures. The genome comprises 8 segments, encoding 9-11 proteins, depending on the type. Influenza A encodes 11 proteins, which includes the surface proteins (hemagglutinin (HA) and neuraminidase (NA), the polymerase complex (PA, PB1 and PB2), nucleoprotein (NP), membrane proteins (M1 and M2), and other proteins (NS1, NS2, NEP). Among the three influenza virus types, influenza A has the highest rate of mutation. Influenza B evolves slower than A, but faster than C. The segmented genome allows gene exchanging between different viral strains, which generate new variants of influenza viruses.

Influenza virus can be transmitted among humans by direct contact with infected individuals or virus-contaminated material. One can also be infected by inhalation of suspended virus droplets in the air. Those droplets are generated by coughing, sneezing or talking of infected individuals. Seasonal influenza is characterized by a sudden onset of high fever, cough (usually dry), headache, muscle and joint pain, severe malaise (feeling unwell), sore throat and runny nose. Cough can be severe and can last two or more weeks. Most people recover from fever and other symptoms within a week without requiring medical attention. But influenza can cause severe illness or death especially in people at high risk as mentioned above. The time from infection to illness, known as the incubation period, is about two days.

The most effective way to prevent the disease and/or severe outcomes from the illness is vaccination. Safe and effective vaccines are available and have been used for more than 60 years. Among healthy adults, influenza vaccines can provide reasonable protection. However, vaccination comes with several limitations. First, influenza vaccine may be less effective in preventing illness among the elderly, and may only reduce severity of disease and incidence of complications and deaths. In addition, influenza vaccination is most effective when circulating viruses are well-matched with vaccine viruses, and the success of vaccination is largely dependent on the good prediction of the most prevalent virus type of the season. Rapid and continual evolution of influenza viral strains through antigenic drift, coupled with the short-lived nature of vaccine-induced immune responses to current influenza vaccines, means that vaccination with seasonally appropriate strains is required every year for prevention.

The current treatment of influenza uses either direct antiviral drugs, or medicines that release the influenza-induced symptoms. There are two classes of influenza antiviral drugs available on the market: neuraminidase inhibitors and M2 channel inhibitors. Neuraminidase inhibitors, oseltamivir or zanamivir, are the primary antiviral agents recommended for the prevention and treatment of influenza. These are effective against both influenza type A and B viruses. Development of resistance to these antiviral drugs has been identified during treatment of seasonal influenza and in sporadic oseltamivir-resistant 2009 H1N1 virus, but the public health impact has been limited to date. M2 channel inhibitors, such as amantadine and rimantadine (amantadanes), are active against influenza A strains, but not influenza B strains. Amantadane resistance among circulating influenza A viruses increased rapidly worldwide beginning during 2003-2004. Therefore, amantadine and rimantadine are not recommended for antiviral treatment or chemoprophylaxis of currently circulating influenza A virus strains.

In 2009, the novel swine H1N1 strain caused an unexpected influenza pandemic as a result of reassortment of genes from human, pig, and bird's H1N1 viruses. This past pandemic, together with the ongoing circulation of highly pathogenic avian H5N1 strains and the recent emergence of the H7N9 virus, a new reassortant of avian origin isolated in China, and associated with severe respiratory disease with 40% of mortality, which could potentially adapt for human-to-human transmission, highlighted the vulnerability of the world population to novel influenza strains. Although vaccination remains the main prophylactic strategy for controlling influenza infection, to bridge the period before a new vaccine becomes available and to treat the severe influenza cases, as well as to counter the problem of viral resistance, a wider choice of anti-influenza drugs is required. Development of new influenza antivirals has therefore again become a high priority and an unmet medical need.

The current invention relates to a compound of formula (I) which can be used for the treatment of, or against viral influenza infections:

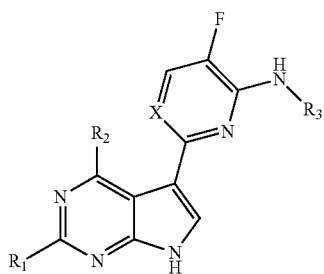

(I)

a stereo-isomeric form, a pharmaceutically acceptable salt, solvate or polymorph thereof, wherein
X is N or C optionally substituted by —CN, —CF$_3$, —C$_{1-3}$ alkyl-N—C(O)—C$_{1-3}$ alkyl,
—C(O)—NH$_2$, —C(O)—NH—C$_{1-3}$ alkyl, —C(O)N-(dialkyl) or —CH$_2$—NC(O)—CH$_3$;
R$_1$ is H or CH$_3$;
R$_2$ is H or NH$_2$;
R$_3$ is C$_{1-8}$ alkyl substituted by carboxylic acid;
   or is C$_{3-8}$ cycloalkyl substituted by carboxylic acid, —N—C$_{1-3}$ alkylsulfone, or
   —N—C(O)—C$_{3-6}$ heterocycle optionally substituted by C$_{1-6}$ alkyl;
   or is C$_{3-6}$ heterocycle substituted by —N—C(O)—C$_{3-6}$ heterocycle.

Preferably the compound according to the invention is the compound according to formula (I) wherein R$_1$ and R$_2$ are both H.

Preferred compounds according to the current invention have the structural formula

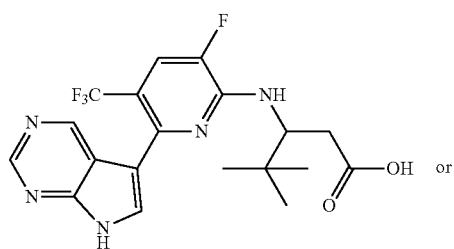

18

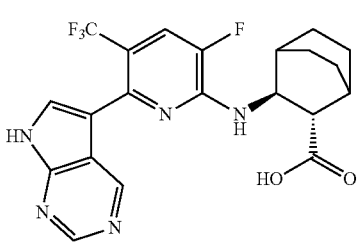

44

Part of the invention is also a pharmaceutical composition comprising a compound of formula (I) or a stereo-isomeric form, a pharmaceutically acceptable salt, solvate or polymorph thereof together with one or more pharmaceutically acceptable excipients, diluents or carriers.

The pharmaceutical composition may also include additional therapeutic agents, like another antiviral agent or an influenza vaccine, or both.

To the invention also belongs a compound of formula (I) or a stereo-isomeric form, a pharmaceutically acceptable salt, solvate or polymorph thereof, or a pharmaceutical composition for use as a medicament.

Additionally the invention relates to a compound of formula (I) or a stereo-isomeric form, a pharmaceutically acceptable salt, solvate or polymorph thereof or a pharmaceutical composition for use in the treatment of influenza.

So part of the invention is the use of a compound represented by the following structural formula (I)

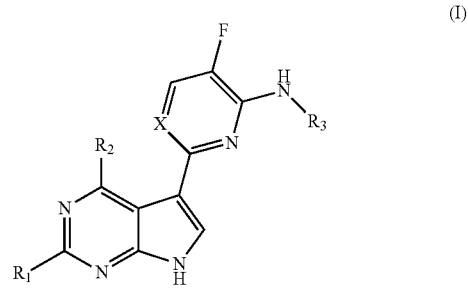

(I)

a stereo-isomeric form, a pharmaceutically acceptable salt, solvate or polymorph thereof, wherein
X is N or C optionally substituted by —CN, —CF$_3$, —C$_{1-3}$ alkyl-N—C(O)—C$_{1-3}$ alkyl,
—C(O)—NH$_2$, —C(O)—NH—C$_{1-3}$ alkyl, —C(O)N-(dialkyl) or —CH$_2$—NC(O)—CH$_3$;
R$_1$ is H or CH$_3$;
R$_2$ is H or NH$_2$;
R$_3$ is C$_{1-8}$ alkyl substituted by carboxylic acid;
   or is C$_{3-8}$ cycloalkyl substituted by carboxylic acid, —N—C$_{1-3}$ alkylsulfone, or
   —N—C(O)—C$_{3-6}$ heterocycle optionally substituted by C$_{1-6}$ alkyl;
   or is C$_m$ heterocycle substituted by —N—C(O)—C$_{3-6}$ heterocycle for inhibiting the replication of influenza virus(es) in a biological sample or patient.

Said use may also comprise the co-administration of an additional therapeutic agent, wherein said additional therapeutic agent is selected from an antiviral agent or influenza vaccine, or both.

The term "alkyl" refers to a straight-chain or branched-chain saturated aliphatic hydrocarbon containing the specified number of carbon atoms.

The term "cycloalkyl" refers to a carbo-cyclic ring containing the specified number of carbon atoms.

The term "heterocycle" refers to molecules that are saturated or partially saturated comprising one or more heteroatoms selected from N, O or S, in particular from N and O. Said heterocycle may have 4, 5, 6 or 7 ring atoms.

Pharmaceutically acceptable salts of the compounds of formula (I) include the acid addition and base salts thereof.

Suitable acid addition salts are formed from acids which form non-toxic salts. Suitable base salts are formed from bases which form non-toxic salts.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral, rectal, or percutaneous administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

EXAMPLES

Preparation of Compounds of Formula (I)

Scheme 1. Preparation of compound 7

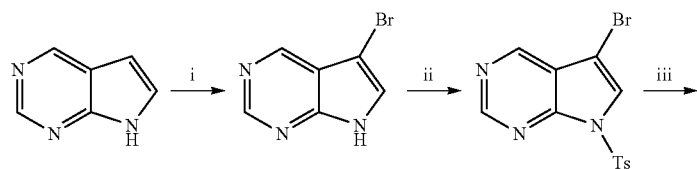

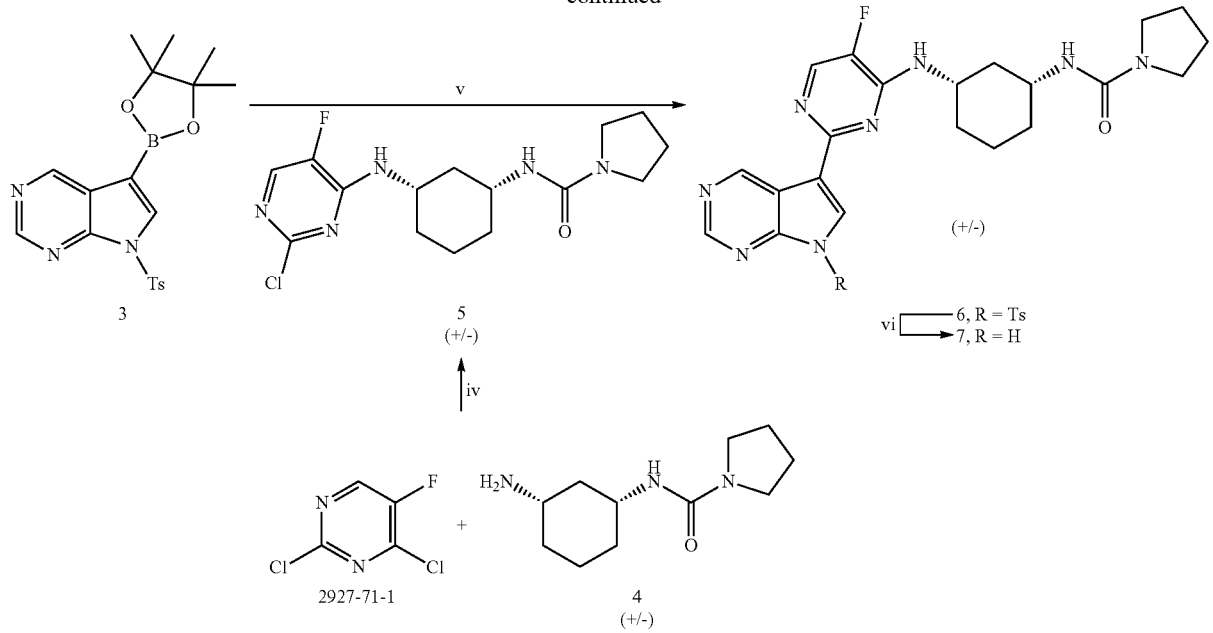

Scheme 1. i) Br₂, DMF, rt, 8 h ii) NaH, TsCl, THF iii) bis(pinacolato)diboron, Pd(dppf)Cl₂, KOAc, 1,4-dioxane, 80° C., 16 h iv) EtOH/THF, DIPEA v) Na₂CO₃, Tetrakis, Xantphos, 1,4-dioxane, microwave 150° C., 15 min vi) NaOCH₃, CH₃OH

Preparation of Intermediate 1

To a stirred solution of 7H-pyrrolo[2,3-d]pyrimidine (11.5 g, 73.92 mmol) in DMF (350 mL) was added bromine (11.8 g, 73.84 mmol) in DMF (50 mL) at 0° C. The cooling bath was removed and the reaction stirred at 20° C. for 8 h, then the reaction mixture was poured into ice-water and basified with Na₂CO₃.

The mixture was extracted with ethyl acetate. The combined organic layers were washed with 10% aq. Na₂S₂O₃, brine, dried over MgSO₄, the solids were removed by filtration, and the filtrate was concentrated under reduced pressure to afford 1, 5-bromo-7H-pyrrolo[2,3-d]pyrimidine as yellow solid, used in the next step without further purification.

$^1$H NMR (400 MHz, DMSO-d₆) δ ppm 7.84 (s, 1 H), 8.84 (s, 1 H), 8.92 (s, 1 H), 12.57 (br, 1 H).

Preparation of Intermediate 2

To a stirred solution of 5-bromo-7H-pyrrolo[2,3-d]pyrimidine (12.8 g, 55.11 mmol) in THF was added NaH (4.48 g, 112.01 mmol) portion wise at 0° C. under nitrogen. The resulting mixture was stirred at 5° C. for 1 hour then p-toluenesulfonyl chloride (11.6 g, 60.85 mmol) was added portion wise. The reaction mixture was allowed to warm to 20° C. and stirred for 3 hours. The reaction mixture was poured into a mixture of ice and 1M aq. HCl while stirring. The mixture was extracted with ethyl acetate. The combined organic layers were washed with brine, dried over MgSO₄, the solids were removed by filtration and the filtrate was concentrated under reduced pressure. The residue was purified by crystallization from ethyl acetate to afford 2, 5-bromo-7-tosyl-7H-pyrrolo[2,3-d]pyrimidine as white solid.

$^1$H NMR (400 MHz, DMSO-d₆) δ ppm 2.36 (s, 3 H), 7.47 (d, J=8.0 Hz, 2 H), 8.06 (d, J=8.0 Hz, 2 H), 8.31 (s, 1 H), 9.03 (s, 1 H), 9.06 (s, 1 H). LC-MS ES⁺ m/z=351.8; Rt: 1.16 min, method D.

Preparation of Intermediate 3

A mixture of 5-bromo-7-tosyl-7H-pyrrolo[2,3-d]pyrimidine (10 g, 28.39 mmol), bis(pinacolato)diboron (14.42 g, 56.79 mmol), potassium acetate (8.36 g, 85.18 mmol), Pd(dppf)Cl₂ (1 g, 1.37 mmol) in 1,4-dioxane (170 mL, degassed with nitrogen) was heated at 80° C. for 16 hours under nitrogen in a 500 mL round bottom flask equipped with a reflux condenser. The reaction mixture was cooled to room temperature, filtered through packed Celite and the solid was rinsed with ethyl acetate. The filtrate was concentrated under reduced pressure and the residue was purified by silica column chromatography using a heptane to ethyl acetate gradient. The desired fractions were collected and concentrated under reduced pressure to afford 3,5-(4,4,5,5-tetramethyl-1,3,2-dioxaborolan-2-yl)-7-tosyl-7H-pyrrolo[2,3-d]pyrimidine.

$^1$H NMR (400 MHz, DMSO-d₆) δ ppm 1.33 (s, 12 H) 2.37 (s, 3 H) 7.47 (d, J=8.36 Hz, 2 H) 8.11 (d, J=8.58 Hz, 2 H) 8.14 (s, 1 H) 9.00 (s, 1 H) 9.10 (s, 1 H). LC-MS ES⁺ m/z=318.1; Rt: 0.74 min, method A.

Preparation of Intermediate 5

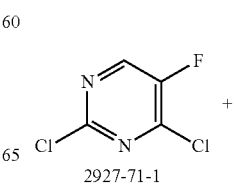

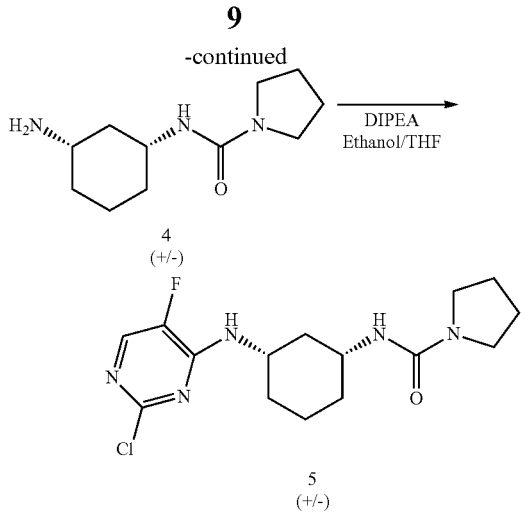

A solution of 2,4-dichloro-5-fluoro-pyrimidine (2.76 g, 16.55 mmol) was stirred at room temperature in ethanol (70 mL) and THF (70 mL). (+/−)-cis-N-(3-aminocyclohexyl)pyrrolidine-1-carboxamide (4.1 g, 16.55 mmol) and DIPEA (8.56 mL, 49.64 mmol) was added drop wise to the reaction mixture and stirred for one hour at 70° C. and then overnight at ambient temperature. The solvent of the reaction mixture was removed under reduced pressure, the residue was reconstituted in water, and extracted twice with DCM. The combined organic layers were washed with water, dried over MgSO$_4$, the solids were removed by filtration and the solvent of the filtrate was removed under reduced pressure. The residue was purified by silica flash column chromatography (gradient: CH$_2$Cl$_2$ to CH$_2$Cl$_2$/CH$_3$OH: 90/10). The desired fractions were pooled and evaporated to dryness to afford 5 as a white solid. LC-MS ES$^+$ m/z=342.3; Rt: 0.75 min, method A.

Preparation of Intermediate 4

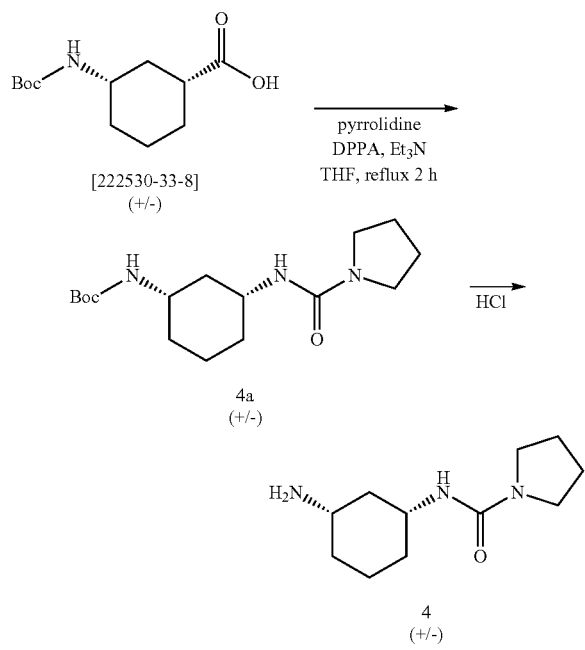

A mixture of (+/−)-cis-3-(boc-amino)cyclohexanecarboxylic acid (9.51 g, 39.09 mmol), diphenyl phosphoryl azide (12.61 mL, 58.63 mmol) and Et$_3$N (7.61 mL, 54.72 mmol) in THF (250 mL) was refluxed for 2 hours. The solution was allowed to reach room temperature, then pyrrolidine (9.81 mL, 117.26 mmol) was added and the mixture was refluxed for 1 hour. The mixture was cooled to 0° C., the precipitate was isolated by filtration and washed with THF, dried in vacuo to afford 4a, t-butyl (+/−)-(cis-3-(pyrrolidine-1-carboxamido)cyclohexyl)carbamate, as a white powder.

A solution of (+/−)-t-butyl (cis-3-(pyrrolidine-1-carboxamido)cyclohexyl)carbamate (23.77 g, 76.33 mmol) in HCl (4 M in 1,4-dioxane, 344 mL) was stirred at room temperature for 4 hours. The solution was concentrated under reduced pressure and then dried in vacuo to afford 4, (+/−)-N-((cis)-3-aminocyclohexyl)pyrrolidine-1-carboxamide as a white solid. LC-MS ES$^+$ m/z=212.2; Rt: 1.06 min, method C.

Preparation of 7

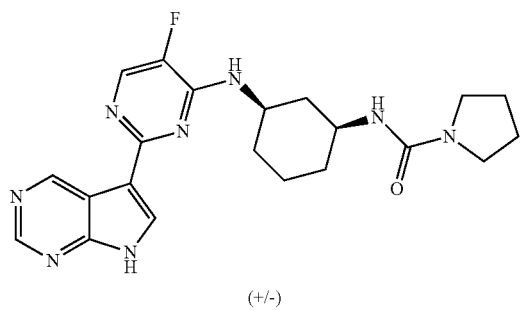

A mixture of 3 (799 mg, 2 mmol), 5 (684 mg, 2 mmol) and Na$_2$CO$_3$ (3 mL, 2 M, 6 mmol) was stirred in 1,4-dioxane (10 mL) at room temperature under a nitrogen atmosphere. Then tetrakis(triphenylphosphine)palladium(0) (116 mg, 0.1 mmol) and Xantphos (58 mg, 0.1 mmol) were added and the mixture was degassed for 10 minutes. The reaction was heated at 150° C. in the microwave for 15 min. The solvents were removed under reduced pressure, and the residue was stirred for one hour with NaOCH$_3$ (100 mL, 0.5 M in CH$_3$OH). The solvent was removed under reduced pressure and the residue was stirred in water and neutralized with acetic acid. The solution was extracted 3 times with CH$_2$Cl$_2$, dried over MgSO$_4$, the solids were removed by filtration and the solvent of the filtrate was removed under reduced pressure. The residue was purified over silica using a gradient of CH$_2$Cl$_2$/CH$_3$OH: 98/2 to 90/10. The best fractions were pooled, the solvent removed under reduced pressure and the product recrystallized from acetonitrile. The off-white precipitate was collected by filtration and dried in vacuo to afford 7.

$^1$H NMR (400 MHz, DMSO-d$_6$) δ ppm 1.06-1.52 (m, 4 H), 1.67-1.89 (m, 6 H), 1.97 (d, J=11.2 Hz, 1 H), 2.06-2.18 (m, 1 H), 3.11-3.23 (m, 5 H), 3.55-3.75 (m, 1 H), 4.02-4.27 (m, 1 H), 5.82 (d, J=7.9 Hz, 1 H), 7.54 (d, J=7.7 Hz, 1 H), 8.10-8.22 (m, 2 H), 8.80 (s, 1 H), 9.59 (s, 1 H). LC-MS ES$^+$ m/z=425.4; Rt: 1.42 min, method B.

Preparation of Intermediate 8

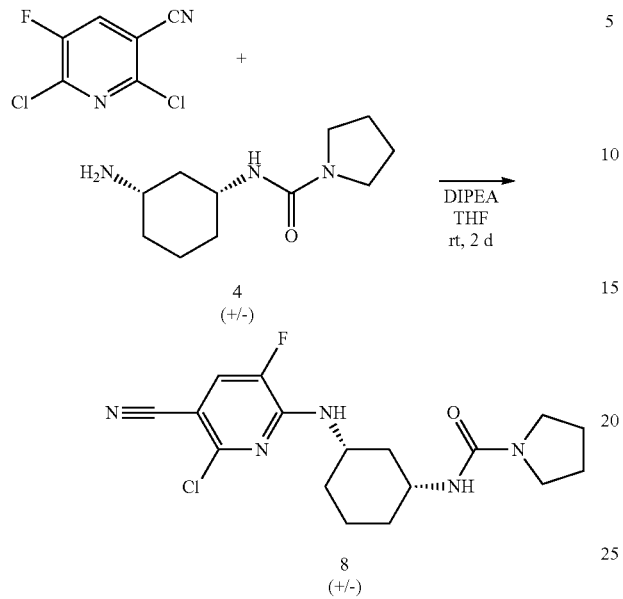

A solution of 2,6-dichloro-5-fluoro-3-pyridinecarbonitrile (4.77 g, 25 mmol) in THF (40 mL) was stirred at room temperature, while a mixture of 4 (6.19 g, 25 mmol) and DIPEA (8.62 mL, 50 mmol) in ACN (20 mL) was added drop wise. The reaction was allowed to stir for 2 days at ambient temperature. The solvent was removed under reduced pressure. The crude was dissolved in diisopropyl-ether/ethyl acetate (1/1) and washed with water. The organic layer was dried (MgSO$_4$), the solids were removed by filtration, and the solvent of the filtrate was removed under reduced pressure. The residue was triturated in diisopropy-lether to afford 8, a white solid, (+/−)-N-((cis)-3-((6-chloro-5-cyano-3-fluoropyridin-2-yl)amino)cyclohexyl)pyrrolidine-1-carboxamide dried in vacuo. LC-MS ES$^+$ m/z=366.1; Rt: 0.88 min, method A.

Preparation of 9

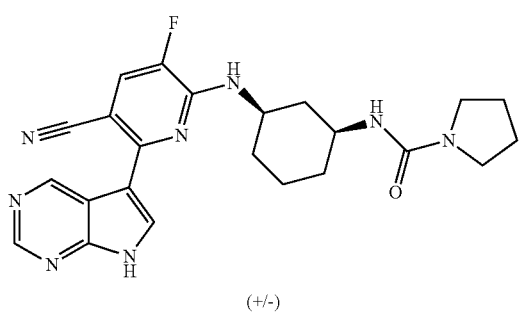

Into a thick-wall glass tube was placed a mixture of 3 (500 mg, 1.25 mmol), Pd(PPh$_3$)$_4$ (145 mg, 0.125 mmol), K$_2$CO$_3$ (346 mg, 2.51 mmol) and 8 (481 mg, 1.32 mmol) in DME (15 mL) and water (5 mL) was heated to 100° C. and stirred for 16 h. The solvent was removed under reduced pressure. The crude residue was stirred in DCM, filtered off and purified by silica flash column chromatography (first gradient: heptane-ethyl acetate; second gradient: DCM-DCM/CH$_3$OH 100-90/10). The desired fractions were collected and evaporated to dryness to afford 9, (+/−)-N-((cis)-3-((5-cyano-3-fluoro-6-(7H-pyrrolo[2,3-d]pyrimidin-5-yl)pyridin-2-yl)amino)cyclohexyl)pyrrolidine-1-carboxamide.

$^1$H NMR (600 MHz, DMSO-d$_6$) δ ppm 1.15-1.31 (m, 2 H) 1.34-1.44 (m, 1 H) 1.48 (q, J=11.93 Hz, 1 H) 1.75-1.78 (m, 4 H) 1.78-1.84 (m, 2 H) 2.00 (d, J=11.30 Hz, 1 H) 2.03-2.06 (m, 1 H) 3.16-3.19 (m, 4 H) 3.53-3.56 (m, 1 H) 4.12-4.15 (m, 1 H) 5.84 (d, J=7.92 Hz, 1 H) 7.74 (d, J=7.04 Hz, 1 H) 7.87 (d, J=11.30 Hz, 1 H) 8.33 (s, 1 H) 8.85 (s, 1 H) 9.56 (s, 1 H) 12.66 (br. s., 1 H). LC-MS ES$^+$ m/z=449.2; Rt: 1.55 min, method B.

Preparation of Intermediate 10

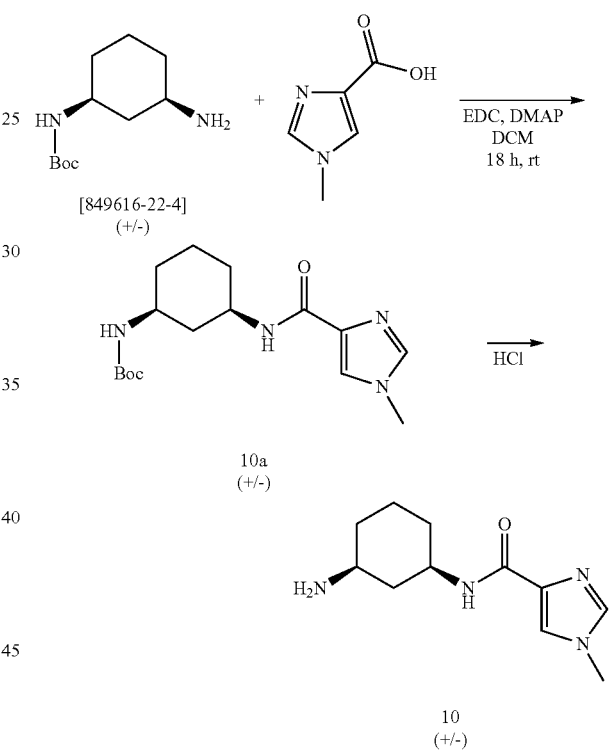

A mixture of (+/−)-tert-butyl ((cis)-3-aminocyclohexyl)carbamate (5 g, 23.3 mmol) and DMAP (7.1 g, 58.3 mmol) in CH$_2$Cl$_2$ (100 mL) was stirred at ambient temperature, then 1-methyl-1H-imidazole-4-carboxylic acid (2.9 g, 23.3 mmol) was added. After stirring for 10 minutes at room temperature, EDC (6.7 g, 35 mmol) was added. The mixture stirred for 18 h at room temperature. The reaction mixture was washed with citric acid (5% aq.), the organic layer was removed, dried (MgSO$_4$), the solids were removed by filtration, and the solvent of the filtrate was removed under reduced pressure to give 10a, (+/−)-t-butyl ((cis)-3-(1-methyl-1H-imidazole-4-carboxamido)cyclohexyl)carbamate. LC-MS ES$^+$ m/z=323.5; Rt: 0.75 min, method A. Removal of the boc-group proceeded via HCl in 1,4-dioxane, as in the method to prepare intermediate 4, to afford 10, (+/−)-N-((cis)-3-aminocyclohexyl)-1-methyl-1H-imidazole-4-carboxamide.

Preparation of Intermediate 11

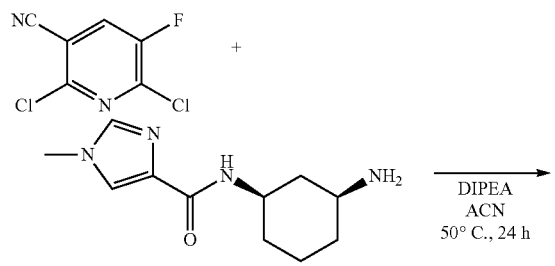

10
(+/-)

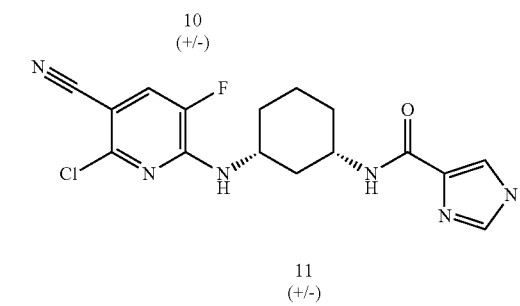

11
(+/-)

A solution of (+/−)-N-[(cis)-3-aminocyclohexyl]-1-methyl-imidazole-4-carboxamide (4.64 g, 15.7 mmol) and 2,6-dichloro-5-fluoro-3-pyridinecarbonitrile (3 g, 15.7 mmol) was stirred at room temperature in ACN (50 mL). DIPEA (10 mL, 54 mmol) was added and the reaction mixture stirred at 50° C. for 24 h. The solvents were removed under reduced pressure. $CH_2Cl_2$ was added and 11, (+/−)-N-((cis)-3-((6-chloro-5-cyano-3-fluoropyridin-2-yl)amino)cyclohexyl)-1-methyl-1H-imidazole-4-carboxamide was isolated via filtration as a white precipitate and was used in the next step without further purification. LC-MS $ES^+$ m/z=377.1; Rt: 1.58 min, method B.

Preparation of 12

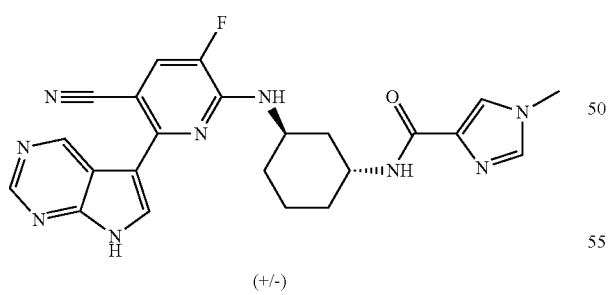

12
(+/-)

Into a 20 mL thick-wall glass vial was placed 3 (0.25 g, 0.63 mmol), Pd(PPh$_3$)$_4$ (72 mg, 0.0626 mmol), $K_2CO_3$ (173 mg, 1.25 mmol), DME (5 mL), water (1.5 mL), and 11 (0.25 g, 0.63 mmol). The vial was sealed and heated in an oil bath at 100° C. for 18 h. The reaction mixture was brought to pH 6 via addition of conc. HCl. DMSO was added and the solution was filtered. The crude was purified by preparatory HPLC (RP SunFire Prep C18 OBD-10 μm, 30×150 mm, mobile phase 0.25% aq. ammonium carbonate, to $CH_3OH$).

The best fractions were pooled and the solvents were removed under reduced pressure to afford 12 as a white solid. $^1$H NMR (400 MHz, DMSO-d$_6$) δ ppm 1.18-1.54 (m, 3 H), 1.62 (q, J=11.7 Hz, 1 H), 1.84 (d, J=10.8 Hz, 2 H), 2.06 (t, J=14.2 Hz, 2 H), 3.67 (s, 3 H), 3.85 (d, J=8.6 Hz, 1 H), 4.20 (dd, J=7.8, 3.6 Hz, 1 H), 7.59 (d, J=1.3 Hz, 1 H), 7.63 (d, J=0.9 Hz, 1 H), 7.68 (d, J=8.4 Hz, 1 H), 7.77 (d, J=7.0 Hz, 1 H), 7.87 (d, J=11.2 Hz, 1 H), 8.33 (d, J=2.4 Hz, 1 H), 8.86 (s, 1 H), 9.59 (s, 1 H), 12.65 (br. s., 1 H). LC-MS $ES^+$ m/z=460.1; Rt: 0.71 min, method A.

Preparation of Intermediate 13

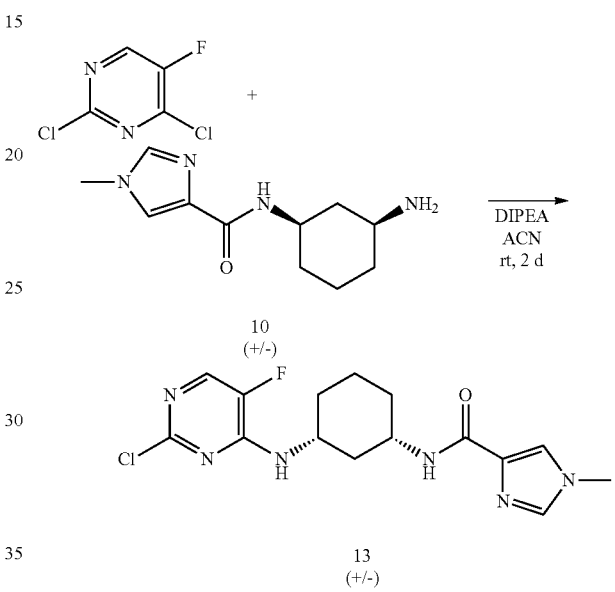

13
(+/-)

A solution of 10 (5.3 g, 18 mmol) and 2,4-dichloro-5-fluoro-pyrimidine (3 g, 18 mmol) was stirred at room temperature in ACN (50 mL). DIPEA (10 mL, 54 mmol) was added and the reaction mixture stirred for 2 days at room temperature. The solvents were removed under reduced pressure, and the crude was purified via silica gel chromatography using a heptane to ethyl acetate gradient. The best fractions were pooled and the solvent removed to afford 13 as an off-white solid. LC-MS $ES^+$ m/z=353.1; Rt: 1.34 min, method B.

Preparation of 14

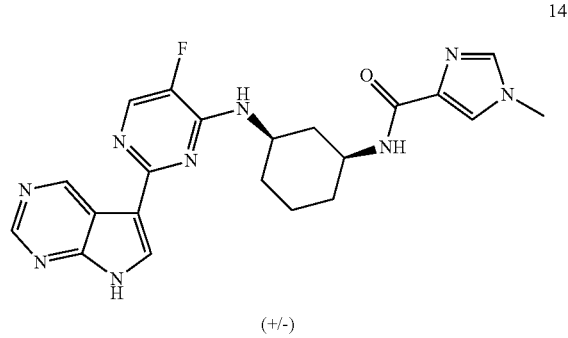 [SMILES: Cn1cnc(C(=O)N[C@H]2CCC[C@@H](Nc3nc(-c4c[nH]c5ncncc45)ncc3F)C2)c1]

14

(+/-)

Intermediate 3 (0.3 g, 0.75 mmol) reacted with 13 (0.265 g, 0.75 mmol) under the same Suzuki reaction conditions as those described for compound 12. The crude was purified by preparatory HPLC (Stationary phase: RP Vydac Denali C18-10 μm, 200 g, 5 cm), mobile phase: 0.25% NH$_4$HCO$_3$ solution in water, CH$_3$OH), the best fractions were pooled and the solvents were removed under reduced pressure to afford 14. $^1$H NMR (400 MHz, DMSO-d$_6$) δ ppm 1.27-1.44 (m, 2 H) 1.54 (m, J=11.70, 11.70, 11.70 Hz, 2 H) 1.84 (m, J=11.00 Hz, 2 H) 2.00 (m, J=12.30 Hz, 1 H) 2.14 (m, J=11.90 Hz, 1 H) 3.67 (s, 3 H) 3.89-4.04 (m, 1 H) 4.21 (m, J=7.80, 3.40 Hz, 1 H) 7.53-7.71 (m, 4 H) 8.10-8.26 (m, 2 H) 8.81 (s, 1 H) 9.62 (s, 1 H) 12.47 (br. s., 1 H). LC-MS ES$^+$ m/z=436.2; Rt: 1.27 min, method B.

Preparation of Intermediate 15

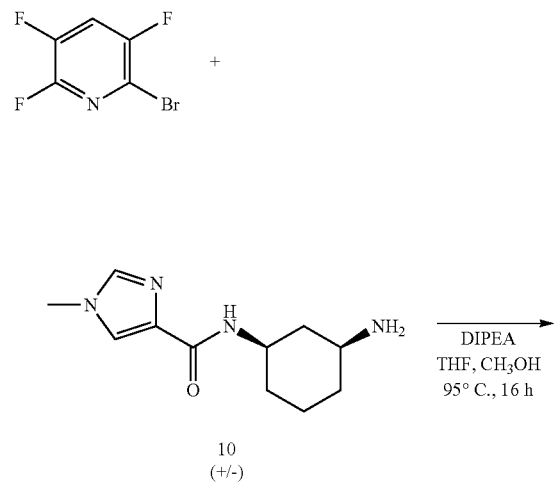

A solution of 2-bromo-3,5,6-trifluoropyridine (3 g, 14.153 mmol), 10 (3.25 g, 18.87 mmol) and DIPEA (3.94 mL, 28.31 mmol) in a mixture of THF/CH$_3$OH (1/1) (50 mL) was heated to 95° C. in a pressure vessel for 16 h. The reaction mixture was dissolved in ethyl acetate with heating and washed with brine. The organic layer was dried (MgSO$_4$), the solids were removed by filtration, and the solvent of the filtrate was concentrated under reduced pressure. The crude was purified by silica flash column chromatography using a heptane to ethyl acetate gradient. The desired fractions were collected and evaporated to dryness to afford 15 as a solid. LC-MS ES$^+$ m/z=414.1; Rt: 0.91 min, method A.

Preparation of 16

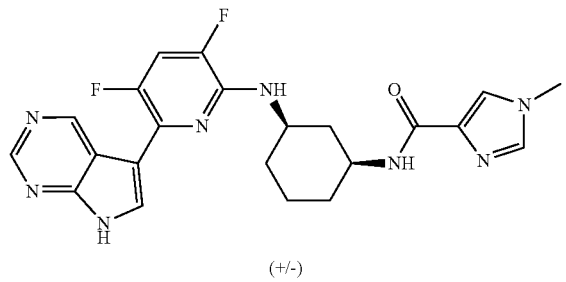

Intermediate 3 (0.20 g, 0.50 mmol) reacted with 15 (0.207 g, 0.50 mmol) under the same Suzuki reaction conditions as those described for the formation of compound 7. The crude was further reacted with NaOCH$_3$ (2.8 mL, 0.5 M in CH$_3$OH) in an ultrasonic bath for 1 h, then the solvent was removed under reduced pressure. The crude was dissolved in ethyl acetate, neutralized with 1M HCl and washed with brine. The organic layer was dried (MgSO$_4$), the solids were removed under reduced pressure to afford a solid. The crude was purified by silica flash column chromatography using a DCM to DCM/CH$_3$OH 100-90/10 gradient. The desired fractions were collected and evaporated to dryness to afford 16. $^1$H NMR (400 MHz, DMSO-d$_6$) δ ppm 1.17-1.42 (m, 2 H) 1.44-1.61 (m, 2 H) 1.76-1.93 (m, 2 H) 2.00-2.21 (m, 2 H) 3.65 (s, 3 H) 3.78-3.95 (m, 1 H) 3.95-4.17 (m, 1 H) 6.46-6.65 (m, 1 H) 7.50-7.79 (m, 4 H) 7.99 (d, J=2.42 Hz, 1 H) 8.71-8.89 (m, 1 H) 9.72 (s, 1 H) 12.46 (br. s., 1 H). LC-MS ES$^+$ m/z=453.0; Rt: 0.72 min, method A Preparation of (+/−)-3-amino-4,4-dimethylpentanate

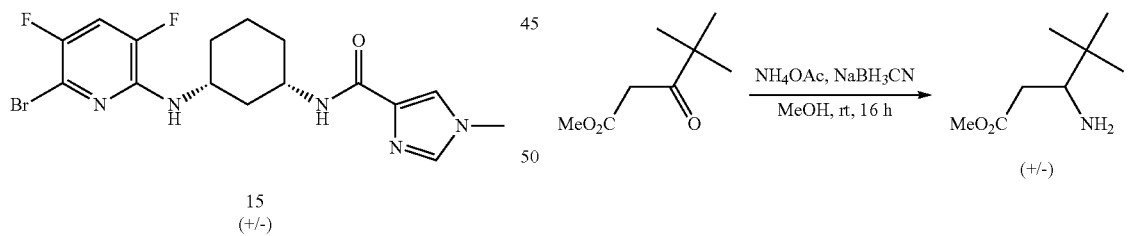

To a solution of methyl 4,4-dimethyl-3-oxopentanoate (2 mL, 12.5 mmol) in methanol (20 mL) was added ammonium acetate (6.75 g, 87.6 mmol) and NaCNBH$_3$ (944 mg, 15.0 mmol). The reaction mixture was stirred at room temperature for 18 h. The mixture was quenched by addition of water and the solvent was removed under reduced pressure. The residue was reconstituted in ethyl acetate and the organic layer was washed with NaOH (aq., 1M), then dried over MgSO$_4$, the solids were removed by filtration and the solvent of the filtrate was removed under reduced pressure to afford (+/−)-3-amino-4,4-dimethylpentanate as colorless liquid that was used without further purification or characterization.

Preparation of Intermediate 17

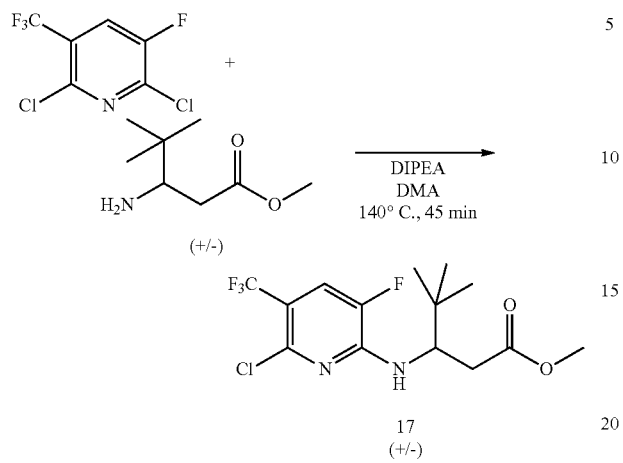

To a solution of 2,6-dichloro-3-fluoro-5-(trifluoromethyl) pyridine (1 g, 4.15 mmol) and (+/−)-3-amino-4,4-dimethyl-pentanate (974 mg, 4.98 mmol) in DMA (5 mL) was added DIPEA (2.86 mL, 16.58 mmol). The mixture was heated in a sealed tube in the microwave at 140° C. for 45 minutes. The reaction mixture was quenched in ice water, and the product was extracted with ethyl acetate. The organic layer was separated, dried (MgSO$_4$), the solids were removed by filtration, and the solvent of the filtrate was removed under reduced pressure. The crude product was purified by silica column chromatography using isocratic dichloromethane. The desired fractions were collected and the solvent was removed to afford 17. LC-MS ES$^+$ m/z=357.2; Rt: 0.92 min, method A.

Preparation of 18

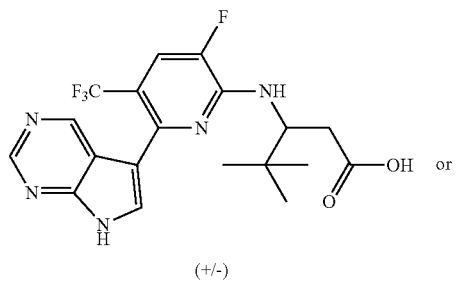

Intermediate 3 (0.35 g, 0.88 mmol) reacted with 17 (0.36 g, 1.02 mmol) under the same Suzuki reaction conditions as those described for the formation of compound 7. The crude was added to NaOCH$_3$ (1.35 mL, 0.5 M in CH$_3$OH) in an ultrasonic bath for 1 h. The solution was diluted with CH$_3$OH (10 mL) and water (10 mL). LiOH (16 mg, 0.67 mmol) was added and the mixture was stirred for 2 h at ambient temperature. The reaction was treated with conc. HCl until pH=4 and the reaction mixture was concentrated under reduced pressure. The crude was purified by preparatory HPLC (stationary phase: RP Vydac Denali C18-10 μm, 200 g, 5 cm, mobile phase: 0.25% NH$_4$HCO$_3$ solution in water, CH$_3$OH). The best fractions were pooled, and the solvent was removed under reduced pressure to afford 18. $^1$H NMR (400 MHz, DMSO-d$_6$) δ ppm 0.76-0.93 (m, 9 H) 2.54-2.61 (m, 2 H) 4.60-4.77 (m, 1 H) 7.35 (d, J=8.58 Hz, 1 H) 7.64-7.81 (m, 1 H) 7.64-7.81 (m, 1 H) 8.82 (s, 1 H) 9.51 (s, 1 H). LC-MS ES$^+$ m/z=426.2; Rt: 1.42 min, method B.

Preparation of 19

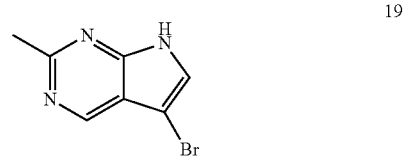

2-methyl-7H-pyrrolo[2,3-d]pyrimidine (426 mg, 3.2 mmol) was dissolved in DMF (54 mL) cooled in an ice bath and treated with N-bromosuccinimide (569 mg, 3.2 mmol) portionwise under nitrogen. The resulting mixture was stirred for 20 minutes, allowed to warm to room temperature and stirred for 10 minutes. The reaction was quenched by the addition of CH$_3$OH (5 mL) and the solvent removed under reduced pressure. The residue was purified by silica flash column chromatography using a heptane to ethyl acetate gradient. The desired fractions were collected and the solvent was removed under reduced pressure to afford 5-bromo-2-methyl-7H-pyrrolo[2,3-d]pyrimidine, 19.

Preparation of Intermediate 20

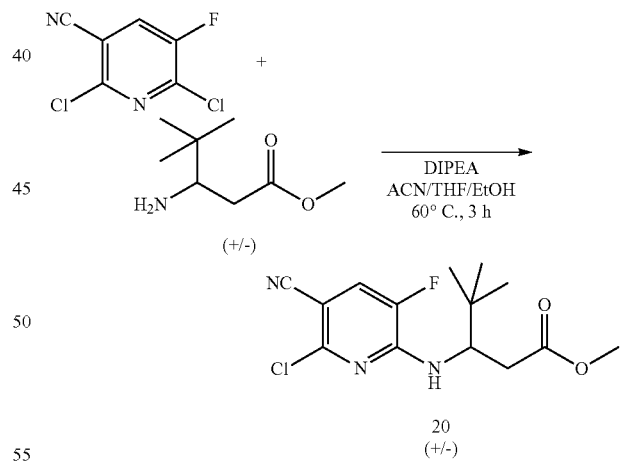

A solution of (+/−)-3-amino-4,4-dimethylpentanate (3.09 g, 13.32 mmol) and 2,6-dichloro-5-fluoronicotinonitrile (3 g, 15.71 mmol) was stirred at room temperature in mixture of acetonitrile/THF/EtOH (50/25/25 mL). DIPEA (5.414 mL, 31.42 mmol) was added and reaction mixture stirred for 3 h at 60° C. The solvents were removed under reduced pressure, and the crude was purified via silica gel chromatography using a heptane to ethyl acetate gradient to afford 20 as a solid. LC-MS ES$^+$ m/z=314.1; Rt: 1.13 min, method A.

Preparation of 21

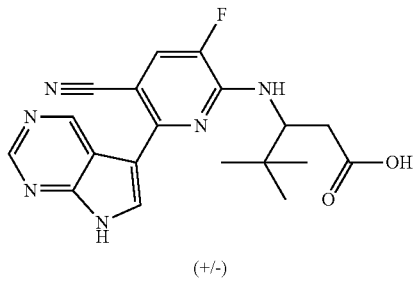

21
(+/-)

Intermediate 3 (0.35 g, 0.88 mmol) reacted with 17 (0.36 g, 1.16 mmol) under the same Suzuki reaction conditions as those described for the formation of compound 7. The crude was added to NaOCH$_3$ (4 mL, 0.5 M in CH$_3$OH) in an ultrasonic bath for 1 h. The solution was diluted with CH$_3$OH (10 mL) and water (10 mL). LiOH (16 mg, 0.67 mmol) was added and the mixture was stirred for 2 h at ambient temperature. The crude was purified by preparatory HPLC (stationary phase: RP Vydac Denali C18-10 μm, 200 g, 5 cm, mobile phase: 0.25% NH$_4$HCO$_3$ solution in water, CH$_3$OH). The best fractions were pooled, and the solvent was removed under reduced pressure to afford 21. $^1$H NMR (400 MHz, DMSO-d$_6$) δ ppm 0.87-0.95 (m, 9 H) 2.54-2.62 (m, 2 H) 4.81 (d, J=5.28 Hz, 1 H) 7.83 (d, J=11.22 Hz, 1 H) 7.87 (d, J=9.02 Hz, 1 H) 8.29 (s, 1 H) 8.85 (s, 1 H) 9.82 (s, 1 H). LC-MS ES$^+$ m/z=383.2; Rt: 0.66 min, method A.

Preparation of 22

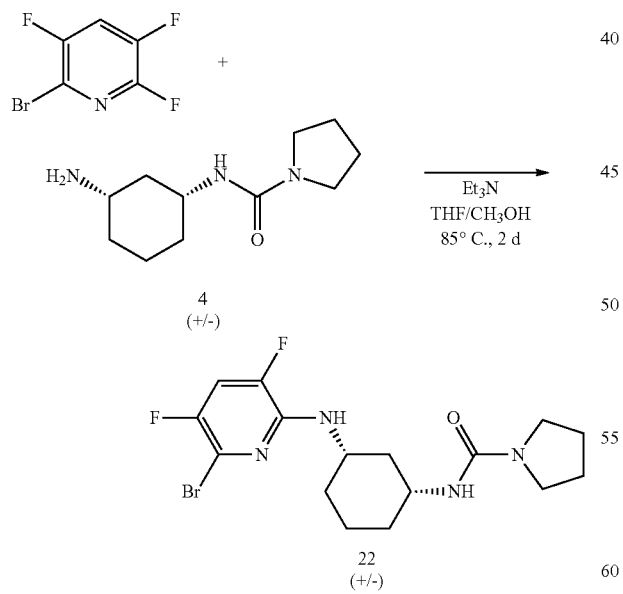

22
(+/-)

A solution of 2-bromo-3,5,6-trifluoropyridine (1.5 g, 7.08 mmol), 4 (1645 mg, 7.78 mmol) and Et$_3$N (1.967 mL, 14.15 mmol) in a mixture of THF/CH$_3$OH (1/1, 50 mL) was heated at 85° C. in a pressure vessel for 2 days. The reaction mixture was concentrated under reduced pressure. The crude was purified by silica flash column chromatography using an heptane to ethyl acetate gradient. The desired fractions were collected and evaporated to dryness to afford intermediate 22. LC-MS ES$^+$ m/z=403.1; Rt: 1.90 min, method B

Preparation of 23

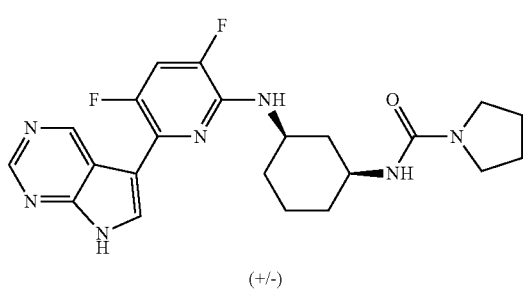

23
(+/-)

Intermediate 3 (0.40 g, 1.0 mmol) reacted with 22 (0.33 g, 0.82 mmol) under the same Suzuki reaction conditions as those described for the formation of compound 7. The crude was added to NaOCH$_3$ (1.5 mL, 0.5 M in CH$_3$OH) in an ultrasonic bath for 1 h. The solvent was removed under reduced pressure. The crude was dissolved in ethyl acetate, neutralized with HCl (1M aq.) and washed with brine. The organic layer was dried (MgSO$_4$), the solids were removed by filtration and the solvent of the filtrate was removed under reduced pressure. The solid was purified by silica flash column chromatography over silica: DCM-DCM/CH$_3$OH (100-90/10). The desired fractions were collected and evaporated to dryness to afford (cis)-methyl 3-((2-chloro-5-fluoropyrimidine-4-yl)amino)bicycle[2.2.2]octane-2-carboxylate, 23. $^1$H NMR (400 MHz, DMSO-d$_6$) δ ppm 1.11-1.33 (m, 2 H) 1.35-1.51 (m, 2 H) 1.71-1.92 (m, 2 H) 1.71-1.92 (m, 4 H) 2.10 (d, J=11.22 Hz, 2 H) 3.18 (t, J=6.60 Hz, 4 H) 3.59 (m, J=7.80, 3.80, 3.80 Hz, 1 H) 3.93-4.11 (m, 1 H) 5.81 (d, J=7.92 Hz, 1 H) 6.51 (d, J=7.26 Hz, 1 H) 7.68 (t, J=10.45 Hz, 1 H) 7.99 (d, J=2.20 Hz, 1 H) 8.82 (s, 1 H) 9.70 (s, 1 H) 12.48 (br. s., 1 H). LC-MS ES$^+$ m/z=441.0; Rt: 1.64 min, method B.

Preparation of 24

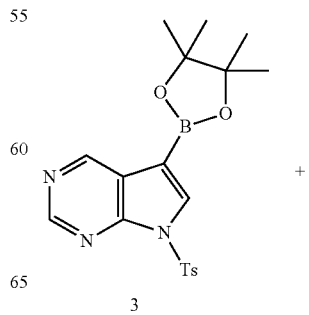

3

-continued

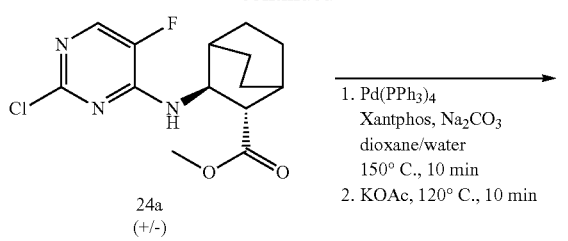

24a
(+/-)

1. Pd(PPh₃)₄
   Xantphos, Na₂CO₃
   dioxane/water
   150° C., 10 min
2. KOAc, 120° C., 10 min 24
(+/-)

24a (283 mg, 0.90 mmol) (for preparation see J. Med. Chem. 2014, DOI: 10.1021/jm5007275) was reacted with intermediate 3 (400 mg, 1.00 mmol) under the same conditions as described in the formation of 7. To the crude mixture was added KOAc (559 mg, 5.69 mmol) in CH₃CN (5 mL) in a vial that was sealed and heated in the microwave at 120° C. for 10 minutes. The solvent was removed under reduced pressure. The compound was dissolved in ethyl acetate and was treated with conc. HCl until pH5. The compound was extracted with ethyl acetate. The organic layer was dried (MgSO₄), the solids were removed by filtration and the solvent of the filtrate was removed under reduced pressure. The crude was purified by preparatory HPLC (stationary phase: RP Vydac Denali C18-10 µm, 200 g, 5 cm), mobile phase: 0.25% NH₄HCO₃ solution in water, CH₃OH), the desired fractions were collected; the solvent was removed under reduced pressure to obtain 24 as a solid. $^1$H NMR (600 MHz, DMSO-d₆) δ ppm 1.22-1.88 (m, 13 H) 1.92 (br. s., 1 H) 1.94 (br. s., 1 H) 1.99 (br. s., 1 H) 2.01 (br. s., 1 H) 2.81 (dd, J=10.27, 2.20 Hz, 1 H) 2.84 (d, J=7.04 Hz, 1 H) 4.34-4.44 (m, 1 H) 4.71 (t, J=6.82 Hz, 1 H) 7.61 (d, J=6.75 Hz, 1 H) 8.11 (d, J=3.81 Hz, 1 H) 8.12 (s, 1 H) 8.14 (s, 1 H) 8.18 (d, J=3.81 Hz, 1 H) 8.34 (s, 1 H) 8.80 (s, 1 H) 8.81 (s, 1 H) 9.64 (s, 1 H) 9.68 (s, 1 H) 10.20 (br. s., 1 H). LC-MS ES⁺ m/z=383.2; Rt: 0.55 min, method A.

Preparation of Intermediate 26

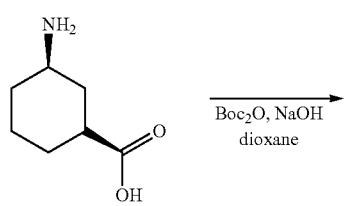

[16636-51-4]

Boc₂O, NaOH
dioxane

-continued

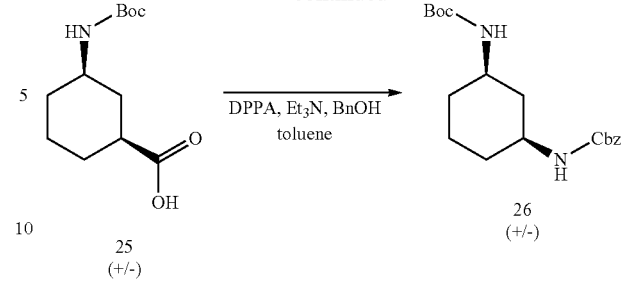

25
(+/-)

DPPA, Et₃N, BnOH
toluene 26
(+/-)

To a suspension of (+/−)-cis-3-aminocyclohexanecarboxylic acid (25 g, 174.6 mmol) in 1,4-dioxane (200 mL) in a 1 L round bottom flask was added 1N NaOH (262 mL, 1 M aq., 262 mmol). After stirring for 15 minutes, the mixture became a clear solution and boc-anhydride (49.54 g, 226.98 mmol) was added. The reaction was stirred at room temperature for 16 hours. The reaction mixture volume was reduced under reduced pressure and the reaction mixture was made acidic (pH 5) with 1M HCl. The formed precipitate was isolated by filtration, washed with water and dried under vacuum to afford 25 as a white solid. $^1$H NMR (400 MHz, DMSO-d₆) δ ppm 0.93-1.31 (m, 4 H), 1.37 (s, 9 H), 1.64-1.75 (m, 2 H), 1.79 (d, J=12.3 Hz, 1 H), 1.95 (d, J=12.3 Hz, 1 H), 2.15-2.30 (m, 1 H), 3.12-3.21 (m, 2 H), 6.75 (d, J=7.9 Hz, 1 H)

Triethylamine (35 mL, 251.6 mmol) and diphenylphosphoryl azide (39.056 mL, 181.09 mmol) were added to a stirred solution of (+/−)-cis-3-[(tert-butoxycarbonyl)amino]cyclohexanecarboxylic acid (38.99 g, 160.25 mmol) in toluene (600 mL), and the resulting mixture was stirred at room temperature for 3 h. Benzyl alcohol (33.17 mL, 320.51 mmol) was added, and the mixture was heated to 100° C. After 12 h, the reaction mixture was cooled to room temperature, diluted with ethyl acetate, and the resulting mixture was washed with brine, dried (Na₂SO₄) and concentrated in vacuo to afford crude solid 26. LC-MS ES⁻ m/z=347.1; Rt: 0.66 min, method B.

Preparation of Intermediate 27

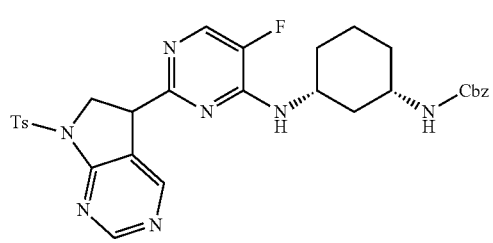

27
(+/-)

Compound 27 was prepared according to the methods to prepare 14. $^1$H NMR (400 MHz, chloroform-d) δ ppm 1.06-1.33 (m, 4 H), 1.61 (d, J=13.4 Hz, 1 H), 1.78 (s, 1 H), 1.87-1.98 (m, 1 H), 2.08 (d, J=12.3 Hz, 1 H), 2.21 (d, J=10.3 Hz, 1 H), 2.38 (s, 3 H), 2.55 (d, J=11.4 Hz, 1 H), 3.65-3.82 (m, 1 H), 4.16-4.31 (m, 1 H), 4.74 (br. s., 1 H), 5.00 (dd, J=7.7, 1.8 Hz, 1 H), 5.05-5.16 (m, 2 H), 7.31 (d, J=8.1 Hz, 6 H), 8.08 (d, J=3.1 Hz, 1 H), 8.16 (d, J=8.4 Hz, 2 H), 8.45 (s, 1 H), 9.05 (s, 1 H)

Preparation of 28

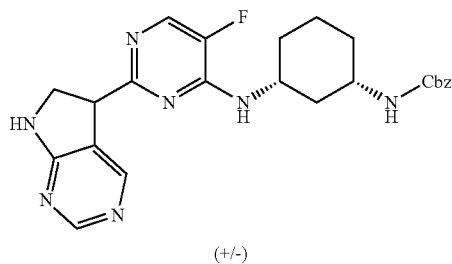

28
(+/-)

Into a 20 mL glass vial, equipped with a magnetic stir bar was placed intermediate 27 (500 mg, 0.81 mmol), CH₃OH (10 mL), and KOAc (250 mg, 2.55 mmol). The vial was sealed and heated to 150° C. for 15 min. in the microwave. The solvent was removed under reduced pressure and the crude product was purified via preparatory HPLC (stationary phase: Uptisphere C18 ODB—10 μm, 200 g, 5 cm, mobile phase: 0.5% NH₄Ac solution in water/10% CH₃CN, CH₃CN). The collected fractions were alkalized with ammonia, reduced in volume under reduced pressure and the precipitate was filtered and washed with water to remove the salt, yielding 28. $^1$H NMR (400 MHz, DMSO-d$_6$) δ ppm 1.05-1.56 (m, 4 H), 1.75-1.91 (m, 2 H), 1.96 (d, J=10.3 Hz, 1 H), 2.14 (d, J=10.6 Hz, 1 H), 3.45-3.62 (m, 1 H), 4.05-4.26 (m, 1 H), 5.00 (s, 2 H), 7.15-7.44 (m, 6 H), 7.56 (d, J=7.7 Hz, 1 H), 8.10-8.26 (m, 2 H), 8.81 (s, 1 H), 9.61 (s, 1 H), 12.48 (br. s., 1 H). LC-MS ES⁺ m/z=462.2; Rt: 1.70 min, method B.

General Method A. Compound 27 was added to TFA at room temperature and allowed to stir for 2 days. The solvents were removed under reduced pressure, and to the residue was added aq. NaHCO₃ and CH₂Cl₂. The organic layer was dried (MgSO₄), the solids were removed by filtration, and the solvent of the filtrate was removed under reduced pressure, then filtered through silica gel. The crude was then mixed with an organic base (Et₃N, or DIPEA) and an electrophile (acid chloride, chloroformate, or isocyanate) at 0° C. to room temperature in THF or acetonitrile. If the reactant was a carboxylic acid, the amide bond could also be formed using a coupling agent (e.g. HATU, EDC) in a polar solvent (e.g. DMF). This was followed by tosyl group removal via addition of excess potassium t-butoxide that was stirred at room temperature for 1 day. The products were purified via silica column chromatography using a CH₂Cl₂ to 10% CH₃OH in CH₂Cl₂ gradient.

Preparation of Intermediate 29a

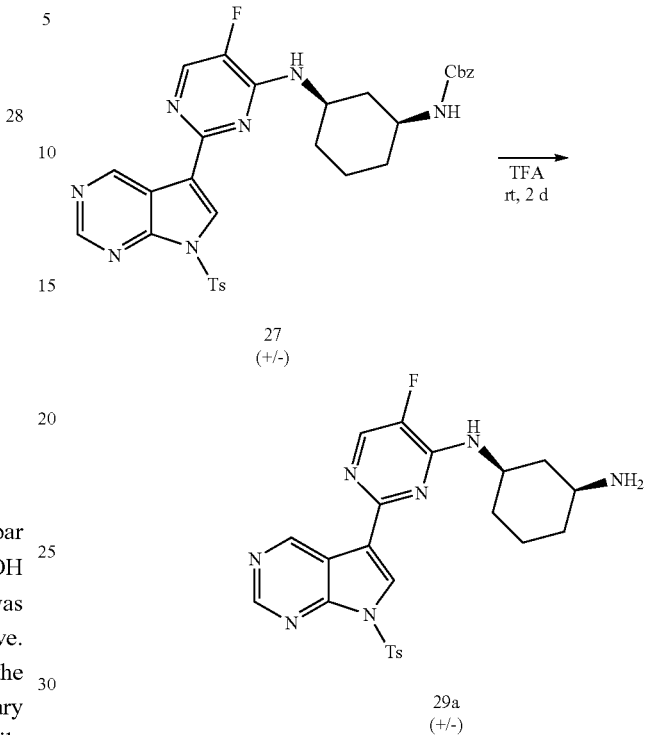

To a reaction flask containing intermediate 27 (3 g, 4.873 mmol) was added to TFA (30 mL) at room temperature. The resulting solution was allowed to stir for 2 days at ambient temperature. The solvent was removed under reduced pressure and NaHCO₃ and CH₂Cl₂ were added. The organic layer was concentrated and dried. The organic layer was dried (MgSO₄), the solids were removed by filtration, and the solvent of the filtrate was removed under reduced pressure. The compound was purified by flash column chromatography using dichloromethane and methanol as eluents. The desired fractions were collected and the solvent was removed under reduced pressure, yielding 29a. LC-MS ES⁺ m/z=482; Rt: 0.77 min, method C.

Preparation of Intermediate 29b

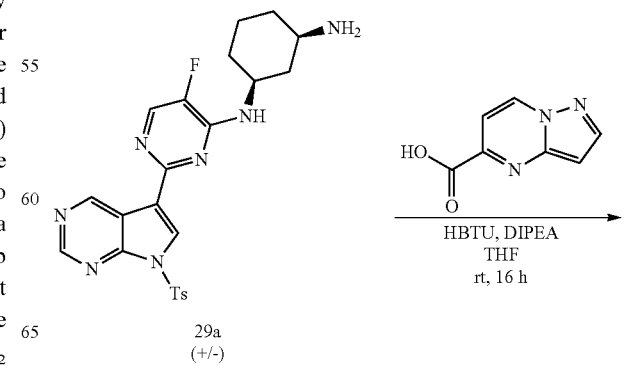

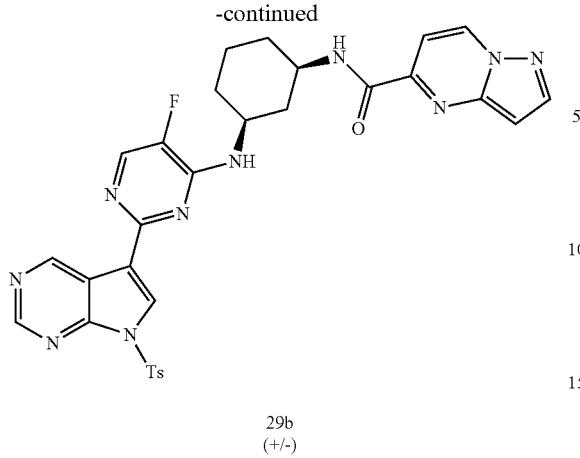

29b
(+/-)

To a reaction flask containing intermediate 29a (100 mg, 0.208 mmol) in THF (4 mL), was added HBTU (285 mg, 0.75 mmol) and N,N-Diisopropylethylamine (0.131 mL, 0.75 mmol). The resulting mixture was stirred at room temperature for 5 minutes under inert atmosphere. Pyrazolo[1,5-a]pyrimidine-5-carboxylic acid (41 mg, 0.25 mmol) was added and the reaction mixture was stirred at room temperature for 16 h. THF was removed under reduced pressure and the resulting residue was extracted with DCM and water. The organic layers were concentrated under reduced pressure, yielding 29b. LC-MS ES$^+$ m/z=627; Rt: 1.26 min, method C.

Preparation of 29

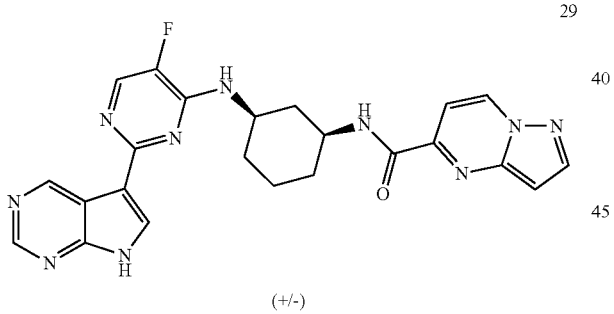

29
(+/-)

To a reaction flask containing 29b (130 mg, 0.207 mmol) dissolved in THF (4 mL), was added potassium tert-butoxide (1.04 mL, 1.04 mmol). The resulting mixture was stirred at room temperature for 24 h. The reaction was quenched with NaHCO$_3$ and CH$_2$Cl$_2$. The organic layer was dried (MgSO$_4$), the solids were removed by filtration, and the solvent of the filtrate was removed under reduced pressure. The compound was purified by flash column chromatography using dichloromethane and methanol as solvents. The desired fractions were collected and the solvent was removed under reduced pressure, yielding 29.

$^1$H NMR (300 MHz, DMSO-d$_6$) δ ppm 1.18-2.09 (m, 8 H) 3.99-4.09 (m, 1 H) 4.25 (br s, 1 H) 6.90 (d, J=1.51 Hz, 1 H) 7.55 (d, J=7.29 Hz, 1 H) 8.17 (d, J=3.85 Hz, 1 H) 8.22 (s, 1 H) 8.37 (d, J=2.20 Hz, 1 H) 8.80 (s, 1 H) 8.83-8.93 (m, 1 H) 9.25 (d, J=7.15 Hz, 1 H) 9.61 (s, 1 H). LC-MS ES$^+$ m/z=473; Rt: 2.16 min, method C.

Preparation of 42

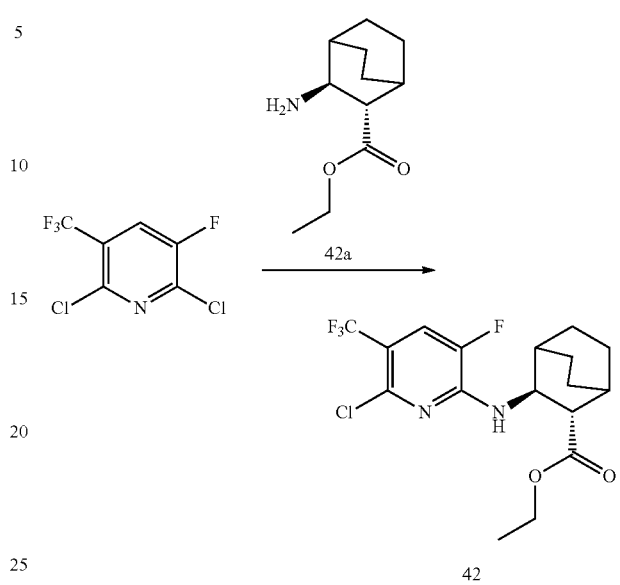

42

Into a 100 mL round bottom flask was placed 2,6-dichloro-3-fluoro-5-(trifluoromethyl)pyridine (2 g, 8.291 mmol), 42a (for preparation see J. Med. Chem. 2014, DOI: 10.1021/jm5007275, 1.822 g, 7.794 mmol), ACN (40 mL), and DIPEA (3.215 g, 24.874 mmol). The resulting mixture was allowed to stir at room temperature for 2 days. The solvent was removed under reduced pressure and the crude was purified via silica column chromatography using a heptane to ethyl acetate gradient. The best fractions were collected and the solvent removed under reduced pressure to afford 42. LC-MS ES$^+$ m/z=394.1; Rt: 1.37 min, method A.

Preparation of 43

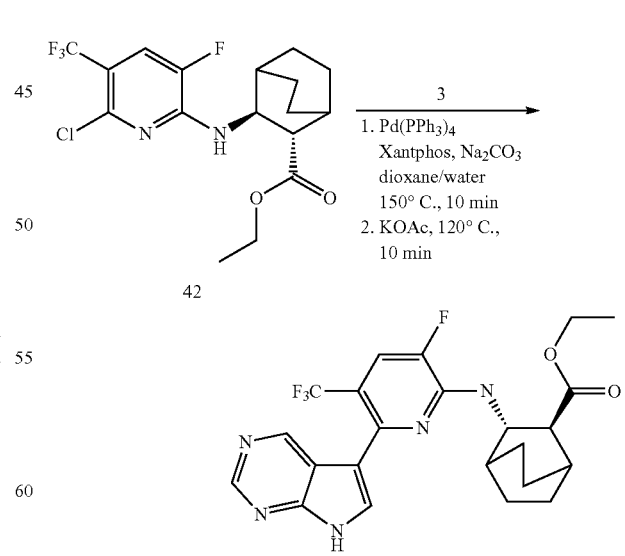

43

A mixture of 3 (400 mg, 0.98 mmol), 42 (400 mg, 0.983 mmol), Pd(PPh$_3$)$_4$ (116 mg, 0.1 mmol), Xantphos (58 mg, 0.1 mmol), Na₂CO₃ (2.8 mL, 2 M aq., 5.77 mmol), and 1,4-dioxane (10 mL) was stirred at 150° C. for 10 minutes under microwave irradiation. The solvent was removed under reduced pressure. DCM was added, then the mixture was filtered through a silica plug and flushed with 5 volumes DCM. The solvent was removed under reduced pressure. KOAc (200 mg) and ethanol (7 mL) were added and heated to 120° C. for 10 min in the microwave. The residue was purified via silica column chromatography using a heptane to ethyl acetate gradient. The best fractions were collected and the solvent removed under reduced pressure, yielding 43.

Preparation of 44

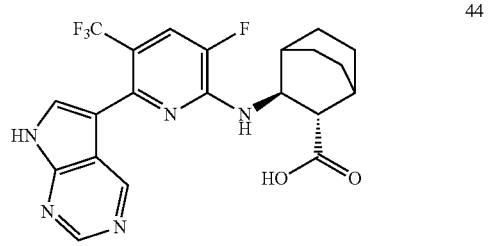 [SMILES: O=C(O)[C@H]1C2CCC(CC2)[C@@H]1Nc1nc(-c2c[nH]c3ncncc23)c(C(F)(F)F)cc1F]

44

In a 100 mL flask 43 (1.6 g, 2.533 mmol) was stirred in 1,4-dioxane (90 mL) at 60° C., while a solution of LiOH (606.6 mg, 25.33 mmol) in water (10 mL) was added. The mixture was brought to reflux for 1 h and was allowed to stir overnight at ambient temperature. 1,4-dioxane was evaporated and the residue was taken in 20 mL ethyl acetate, stirred and neutralized with HCl conc. The residue was concentrated under reduced pressure. A purification was performed via preparatory HPLC (stationary phase: RP XBridge Prep C18 ODB-5 μm, 30×250 mm, mobile phase: 0.25% NH₄HCO₃ solution in water, methanol). The desired fractions were collected and evaporated to dryness. After addition of methanol the solution was concentrated a second time to afford 44 as a white solid. ¹H NMR (400 MHz, DMSO-d₆) δ ppm 1.27-1.45 (m, 4 H) 1.75 (m, 4 H) 1.78-1.86 (m, 1 H) 1.91-2.01 (m, 1 H) 2.74 (m, 1 H) 4.64 (m, 1 H) 7.42 (m, 1 H) 7.70-7.76 (m, 2 H) 8.82 (s, 1 H) 9.37 (s, 1 H). LC-MS ES⁺ m/z=449; Rt: 1.58 min, method B.

Preparation of 46

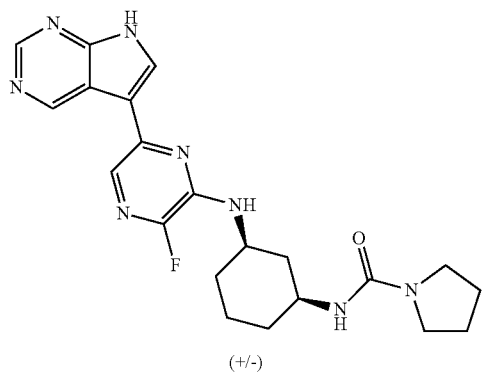

46

(+/-)

Compound 46 was prepared according to the methods to prepare 7. LC-MS ES⁺ m/z=424.2; Rt: 1.41 min, method B.

Preparation of 48

Compound 14 was purified via preparatory SFC (stationary phase: Chiralcel Diacel OD 20×250 mm, mobile phase: CO₂, isopropanol with 0.2% isopropylamine). The desired fractions were collected and the solvent was removed under reduced pressure, yielding 48

Preparation of 50

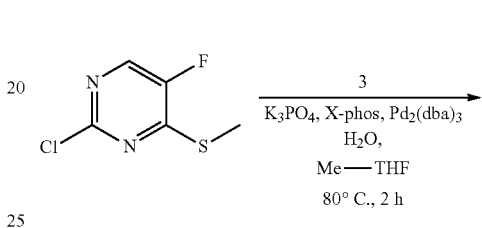

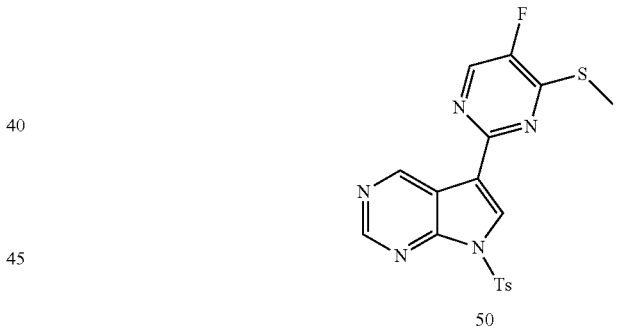

50

A mixture of 3 (4.39 g, 11 mmol), 2-chloro-5-fluoro-4-methylsulfanyl-pyrimidine (1.96 g, 11 mmol) and potassium phosphate (7 g, 33 mmol) was stirred in water (44 mL) and Me-THF (132 mL) at room temperature under a nitrogen atmosphere. Then Xantphos (629 mg, 1.32 mmol) and Pd₂(dba)₃ (302.19 mg, 0.33 mmol) were added and degassing was done for ten minutes with nitrogen bubbling through the mixture. The reaction was heated to 80° C. and stirred for two hours at this temperature in a closed vessel. The mixture was allowed to cool down for one hour, then reconstituted in 200 mL ethyl acetate and twice washed with brine. The organic layer was dried over MgSO₄, filtered and evaporated. The residue was purified over silica with dichloromethane/methanol (99/1) as eluent. The desired fractions were evaporated and the residue was crystallized in acetonitrile. The crystals were collected by filtration and dried in vacuo, 50. LC-MS ES⁺ m/z=415; Rt: 2.00 min, method B.

Preparation of 51

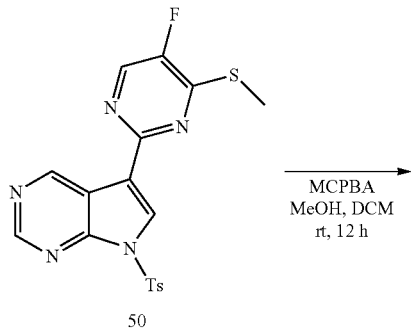

A solution of 50 (415.47 mg, 1 mmol) in methanol (2 mL) and DCM (1.15 mL) was stirred at room temperature. m-CPBA (739.58 mg, 3 mmol) was added portion wise over a period of ten minutes and stirring was continued overnight at ambient temperature. The mixture was diluted with 30 mL DCM and twice washed with saturated sodium bicarbonate solution in water and once with water. The organic layer was dried over MgSO$_4$, filtered and evaporated. The residue was triturated in diisopropylether/acetonitrile (20/1). The yellow precipitate was collected by filtration and dried, yielding 51. LC-MS ES$^+$ m/z=447; Rt: 1.59 min, method B.

General Method B. Compound 51 was added to 1,4-dioxane at room temperature. The crude was then mixed with an organic base (Et$_3$N or DIPEA) and an amine. The resulting mixture was brought to reflux and stirred for 1 day. The solvent was removed under reduced pressure. The resulting crude was purified via silica column chromatography. This was followed by tosyl group removal via addition of excess potassium t-butoxide that was stirred at room temperature for 1 day. The products were purified via silica gel column chromatography.

Preparation of 52

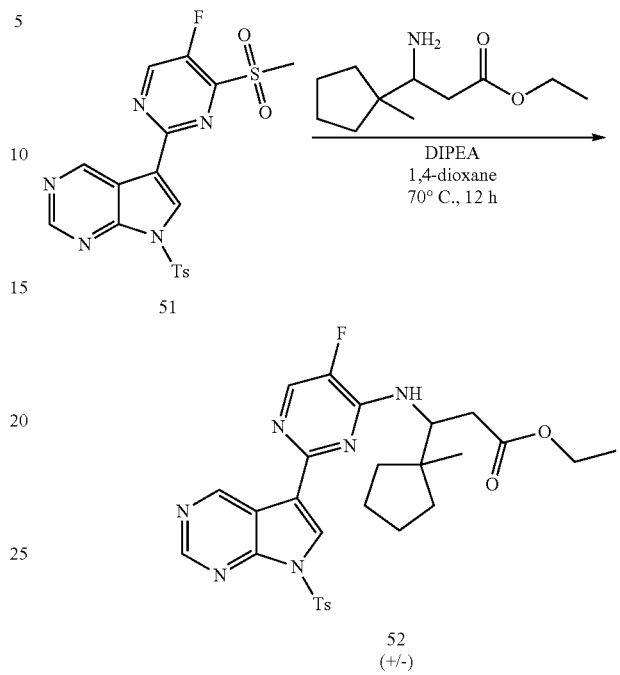

To a solution of 51 (1.683 g, 3.76 mmol) and DIPEA (2 mL) in 1,4-dioxane (30 mL) was added 3-amino-3-(1-methyl-cyclopentyl)-propionic acid ethyl ester (1.500 g, 7.527 mmol). The resulting reaction mixture was stirred at 70° C. overnight. Then, the reaction mixture was evaporated to dryness and purified via silica column chromatography (heptane:ethyl acetate 60:40) to afford 52.

Preparation of
3-amino-3-(1-methyl-cyclopentyl)-propionic acid
ethyl ester

Step 1. Under nitrogen, LiHMDS (1M in THF) (189 mL, 189 mmol) was added dropwise to a solution of cyclopentanecarbonitrile (15 g, 158 mmol) in THF (64 mL) at −78° C. The mixture was then stirred at 30 min and CH$_3$I (14.7 mL, 240 mmol) was added in one portion and the mixture was slowly warmed to rt overnight. EtOAc (250 mL) was added and NH$_4$Cl 10% (200 mL) was slowly added at 0° C. Then water (100 mL) was added to form a solution and the organic layer was separated and washed with brine, dried and concentrated to give 1-methylcyclopentanecarbonitrile (16.8 g, yellow oil) that was used without purification in the next step.

Step 2. At −78° C. under nitrogen, DIBAL (37 mL, 37 mmol) was added dropwise to a solution of 1-methylcyclopentanecarbonitrile (2.0 g, 18 mmol) in CH$_2$Cl$_2$ (117 mL) and the mixture was stirred 15 min at −78° C. after the end of addition. CH$_3$OH (37 mL) was added slowly at −78° C. and the reaction warmed to rt. NaOH (1M) 200 mL was added and the aqueous solution was extracted twice with CH$_2$Cl$_2$, dried over MgSO$_4$ and concentrated. This mixture was stirred for 1 h in HCl aq. (3M), extracted with CH$_2$Cl$_2$, dried over MgSO$_4$ and concentrated to give 1-methylcyclopentanecarbaldehyde (1.4 g, yellow oil).

Step 3. 1-methylcyclopentanecarbaldehyde (1.4 g, 12 mmol), malonic acid (1.0 g, 9.6 mmol), NH$_4$OAc (1.5 g, 19 mmol) in EtOH (5.6 mL) was stirred overnight at 80° C. in a sealed tube. The mixture was cooled to rt, filtered and washed with EtOH. H$_2$SO$_4$ (0.51 mL, 9.6 mmol) was added to the filtrate and the mixture was stirred for 2 h at 80° C. The mixture was concentrated, taken in water and washed with DCM (3×). The organic mixture was discarded and the aqueous layer was basified with NaOH (3N) and extracted with DCM. The organic layer was dried over MgSO$_4$, filtered and concentrated to give 3-amino-3-(1-methyl-cyclopentyl)-propionic acid (0.75 g, colorless oil).

Step 4. 3-amino-3-(1-methyl-cyclopentyl)-propionic acid was mixed with ethanol and to it was added dropwise SOCl$_2$ at 0° C. After addition, the reaction mixture was heated to reflux and stirred for 6 hours. The solvent was removed under reduced pressure. The crude was dissolved in DCM and washed with aq. sat. NaHCO$_3$. The organic layer was dried over MgSO$_4$, filtered and evaporated to dryness to afford 3-amino-3-(1-methyl-cyclopentyl)-propionic acid ethyl ester that was used in the next step with further purification.

Preparation of 53

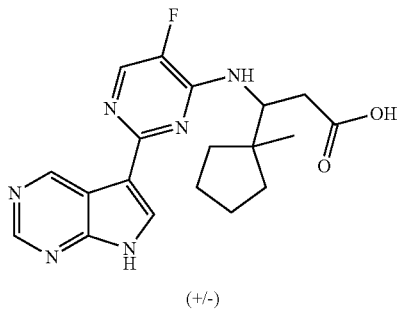

(+/−)

To a closed vessel containing 52 (400 mg, 0.706 mmol) was added potassium t-butoxide (3.63 mL, 3.63 mmol) and THF (10 mL) under inert atmosphere. The mixture was stirred at room temperature for 1 hour. Afterwards, a small amount of water (10 µL) was added and the reaction mixture was heated to 60° C. The solvent of the reaction mixture was evaporated to dryness and purified by preparatory HPLC (Method: From 90% [Aqueous phase]-10% [Organic phase] to 54% [AP]-46% [OP]. AP: 25 mM NH$_4$HCO$_3$ OP: MeCN:methanol 1:1). The desired fractions were collected and the solvent was removed under reduced pressure, yielding 53.
$^1$H NMR (400 MHz, DMSO-d$_6$) δ ppm 1.04 (s, 3 H) 1.17-1.43 (m, 2 H) 1.54-1.69 (m, 5 H) 1.73-1.83 (m, 1 H) 2.55-2.61 (m, 2 H) 4.87-4.94 (m, 1 H) 7.01-7.10 (m, 1 H) 8.04 (s, 1 H) 8.10 (d, J=3.96 Hz, 1 H) 8.77 (s, 1 H) 9.69 (s, 1 H). LC-MS ES$^+$ m/z=384.5; Rt: 1.24 min, method B.

Preparation of Intermediate 59

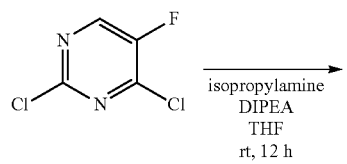

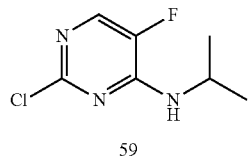

59

A solution of isopropylamine (2.66 mL, 29.95 mmol) and DIPEA (5.16 mL, 29.95 mmol) in THF (50 mL) was stirred at −10° C., while 2,4-dichloro-5-fluoropyrimidine (5 g, 29.95 mmol) was added portion wise. The resulting mixture was stirred at ambient temperature overnight. The mixture was diluted with 100 mL ethyl acetate and 50 mL diisopropylether. This solution was twice washed with water. The organic phase was dried over MgSO$_4$, filtered and evaporated, yielding 67. The residue was used as such. LC-MS ES$^+$ m/z=189; Rt: 1.65 min, method B.

Preparation of 60

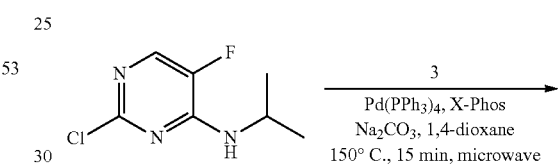

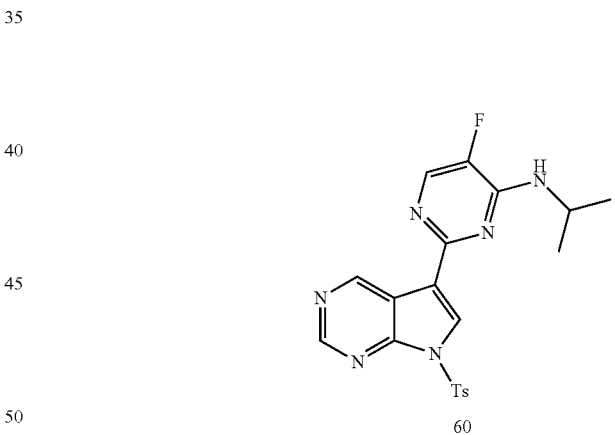

60

A mixture of 3 (798.6 mg, 2 mmol), 59 (379.24 mg, 2 mmol) and Na$_2$CO$_3$ (3 mL, 2 M, 6 mmol) was stirred in 1,4-dioxane (10 mL) at room temperature under a nitrogen atmosphere. Then Pd(PPh$_3$)$_4$ (115.56 mg, 0.1 mmol) and Xantphos (57.86 mg, 0.1 mmol) were added and degassing was done for ten minutes with nitrogen bubbling through the mixture. The reaction was heated to 150° C. under microwave radiation for 15 minutes. The mixture was diluted with water and twice extracted with ethyl acetate. The organic layer was once washed with brine, dried over MgSO$_4$, filtered, and evaporated. The residue was crystallized in diisopropylether with about 10% acetonitrile. The off-white precipitate was collected by filtration and dried in vacuo, yielding 60. LC-MS ES$^+$ m/z=426; Rt: 2.22 min, method B.

Preparation of 61

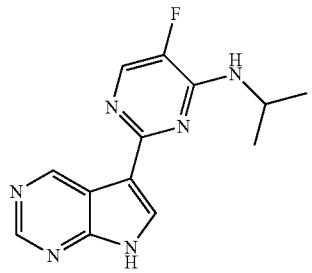

A mixture of 60 (300 mg, 0.7 mmol) and NaOMe (15 mL, 0.5 M, 7.5 mmol) was sonicated for 10 minutes, and stirred for one hour at room temperature. The mixture was evaporated and reconstituted in ice water, stirred and neutralized with 7.5 mL 1N aq. HCl. The water layer was extracted three times with dichloromethane. The combined organic layers were dried over MgSO$_4$, filtered and evaporated. The residue was purified via silica column chromatography using dichloromethane/methanol (98/2-95/5) as gradient. The corresponding fractions were evaporated and the residue was crystallized in diisopropylether/acetonitrile (2/1). The crystals were collected by filtration and dried in vacuo, yielding 61 $^1$H NMR (360 MHz, DMSO-d$_6$) δ ppm 1.29 (d, J=6.59 Hz, 6 H) 4.40-4.51 (m, 1 H) 7.49 (br d, J=7.68 Hz, 1 H) 8.15-8.18 (m, 2 H) 8.82 (s, 1 H) 9.61 (s, 1 H) 12.51 (br s, 1 H). LC-MS ES$^+$ m/z=272.1; Rt: 1.45 min, method B.

Preparation of methyl 3-amino-4,4-dimethylpentanoate

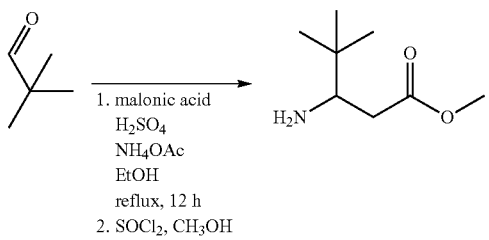

A mixture of trimethylacetaldehyde (33.25 g, 386.027 mmol), malonic acid (30.204 g, 290.246 mmol), NH$_4$OAc (44.746 g, 580.492 mmol) in 100 mL EtOH was refluxed for 6 h. The precipitate was isolated by filtration and washed with ethanol. The solution was used as such and H$_2$SO$_4$ (15.5 mL) was added. The resulting mixture was heated to reflux for 5 hours. The solvent was removed under reduced pressure and the crude was added to 300 mL water and 150 mL Et$_2$O. The aqueous layer was neutralized with NaOH 6N aq. The product was extracted with EtOAc. The organic phase was dried over Na$_2$SO$_4$, filtered and concentrated under reduced pressure.

The residue (10 g, 68.87 mmol) in methanol (50 mL) was cooled on an ice bath and SOCl$_2$ (5 mL, 68.87 mmol) was added drop wise. After addition, the reaction mixture was heated to reflux and stirred for 6 hours. The reaction was complete and the solvent was removed under reduced pressure. The crude was dissolved in DCM and washed with an aq. sat. NaHCO$_3$ and brine. The organic layer was dried over MgSO$_4$, filtered and evaporated to dryness to afford, methyl 3-amino-4,4-dimethylpentanoate.

Preparation of 67

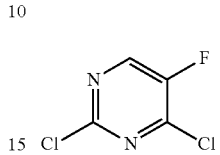 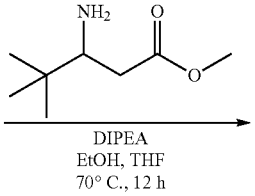

A solution of 2,4-dichloro-5-fluoro-pyrimidine (3 g, 17.967 mmol) was stirred at room temperature in EtOH (72 mL) and THF (72 mL). Methyl 3-amino-4,4-dimethylpentanoate (3.622 g, 22.749 mmol) and DIPEA (9.289 mL, 53.90 mmol) was added drop wise to the reaction mixture and stirred for one hour at 70° C., then overnight at ambient temperature. The reaction mixture was evaporated. The residue was reconstituted in water, and extracted twice with DCM. The combined organic layers were once washed with water, dried over MgSO$_4$, filtered and evaporated. The residue was purified by flash column chromatography over silica (eluent: DCM-DCM/methanol (100-90/10)). The desired fractions were collected and evaporated to dryness to afford, 67. LC-MS ES$^+$ m/z=289.1; Rt: 0.99 min, method A.

Preparation of 68

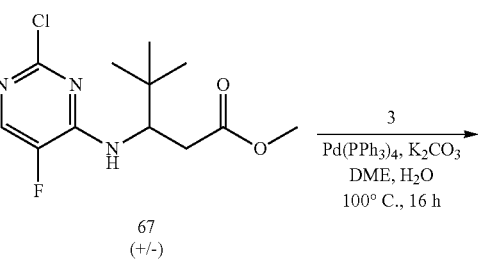

Preparation of 70

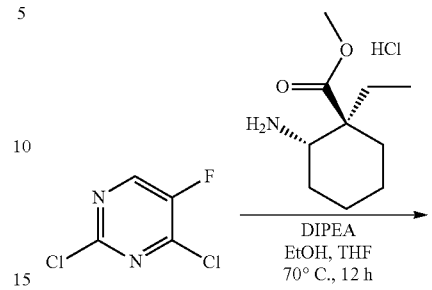

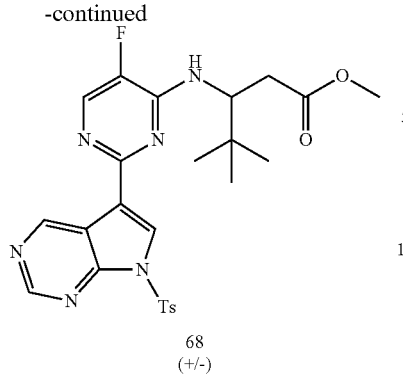

68
(+/-)

In a pressure tube, a mixture of 3 (3.5 g, 8.766 mmol), Pd(PPh$_3$)$_4$ (1013 mg, 0.877 mmol), K$_2$CO$_3$ (2423 mg, 17.53 mmol)) and 67 (2.667 g, 9.204 mmol) in DME (50 mL) and water (15 mL) was heated to 100° C. and stirred for 16 hours. The reaction was completed and the solvent was removed under reduced pressure. The crude residue was taken in DCM and filtered. The filtrate was purified by flash column chromatography over silica (gradient: heptane-EtOAc (100-100)). The desired fractions were collected and evaporated to dryness. The residue was dissolved in a mixture of DCM/methanol (1/1) and purified via silica gel column chromatography (gradient: heptane-EtOAc (100-100)). The desired fractions were collected and the solvent was removed under reduced pressure, yielding 68. $^1$H NMR (400 MHz, DMSO-d$_6$) δ ppm 0.97 (s, 9 H) 2.65 (m, 1 H) 2.78 (m, 1 H) 3.44 (s, 3 H) 4.76-4.94 (m, 1 H) 7.41 (m, 1 H) 8.07-8.27 (m, 2 H) 8.82 (s, 1 H) 9.73 (s, 1 H) 12.47 (br. s., 1 H). LC-MS ES$^+$ m/z=372.2; Rt: 0.84 min, method A.

Intermediate 70 was prepared according to the methods to prepare 67. LC-MS ES$^+$ m/z=315; Rt: 1.11 min, method A.

Preparation of 69

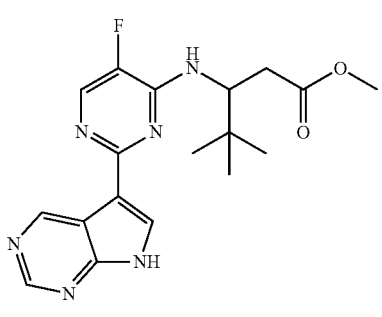

69
(+/-)

A solution of 68 (150 mg, 0.39 mmol) and LiOH (37.379 mg, 1.561 mmol) in water (4 mL) and 1,4-dioxane (8 mL) was stirred at room temperature for 16 hours. The organic solvent was removed under reduced pressure and the water layer was acidified with HCl 1N. The formed precipitate was filtered off, washed with water and dried under vacuo at 50° C. to afford 69. $^1$H NMR (400 MHz, DMSO-d$_6$) δ ppm 0.96 (s, 9 H) 2.54-2.62 (m, 2 H) 4.68-4.84 (m, 1 H) 7.69 (m, 1 H) 8.11-8.15 (m, 2 H) 8.81 (s, 1 H) 9.73 (s, 1 H). LC-MS ES$^+$ m/z=358.1; Rt: 1.15 min, method B.

Preparation of 71

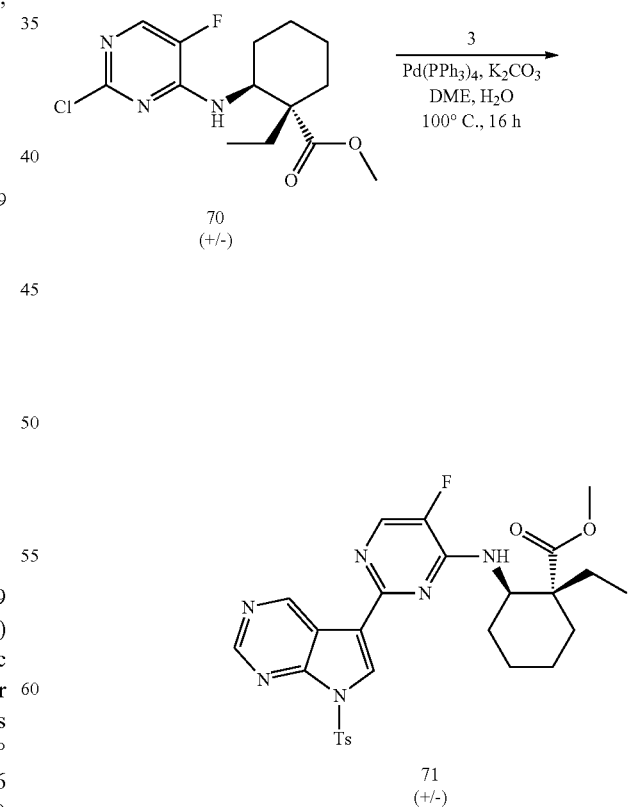

71 was prepared according to the methods to prepare 68.

Preparation of 87

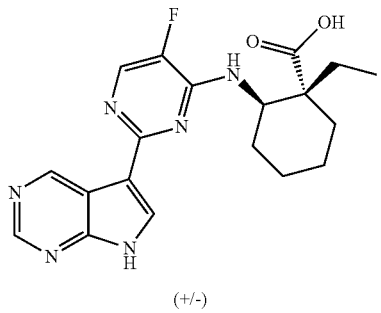

72

(+/-)

Intermediate 72 was prepared according to the methods to prepare 69. LC-MS ES+ m/z=358.1; Rt: 1.15 min, method B.

Preparation of Intermediate 74

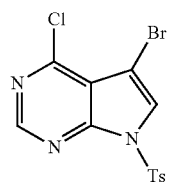

74

Intermediate 74 was prepared according to the methods to prepare intermediate 2.

Preparation of 75

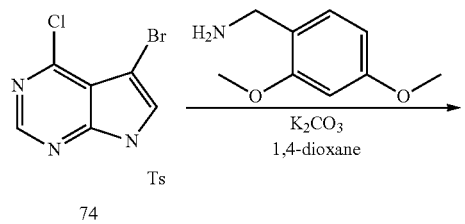

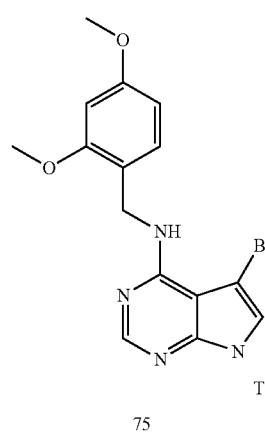

75

A solution of 74 (580 mg, 1.5 mmol), 2,4-dimethoxybenzylamine (276 mg, 1.65 mmol), and K$_2$CO$_3$ (414 mg, 3 mmol) in 1,4-dioxane (6 mL) was stirred for 2 h at 80° C. The reaction mixture was allowed to reach room temperature and the solvent was removed under reduced pressure. The crude reaction mixture was purified by flash column chromatography over silica. (Gradient: petroleum ether-EtOAc (100-50/50)). The desired fractions were collected and evaporated to dryness to afford 75.

Preparation of 76

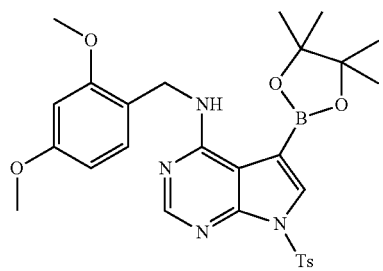

76

76 was prepared according to the methods to prepare intermediate 3.

Preparation of 77

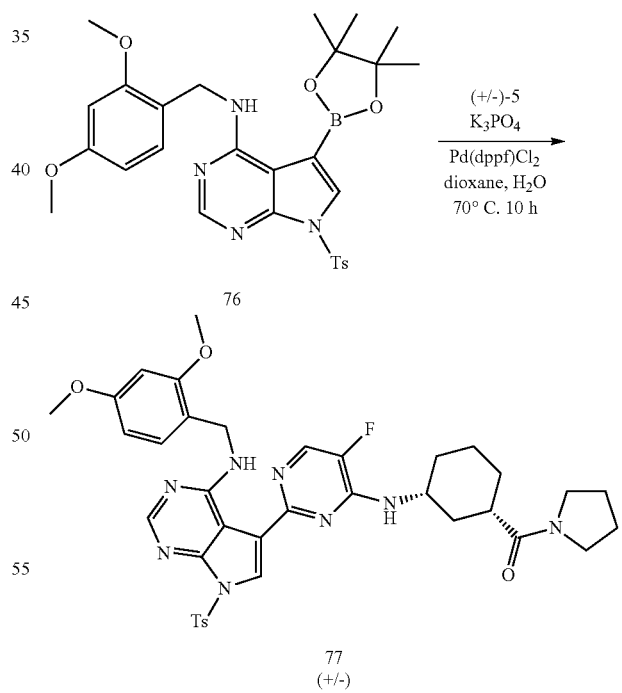

77
(+/-)

A mixture of 76 (2.73 g, 1.47 mmol), 5 (0.5 g, 1.47 mmol), K$_3$PO$_4$ (0.62 g, 2.93 mmol), and [1,1'-Bis(di-tert-butylphosphino)ferrocene]dichloropalladium(II) (96 mg, 0.147 mmol) in 1,4-dioxane (80 mL) and water (20 mL) was heated to 70° C. for 10 h. The reaction mixture was filtered over Celite and concentrated. Then, the reaction mixture was diluted with DCM and washed with water. The organic layer was dried over MgSO₄, and purified by reverse phase HPLC (Column: SYNERGI 250×50 10 μm, Flow rate: 80 mL/min, Mobile Phase A: water (containing 0.1% TFA), Mobile Phase B: Acetonitrile, Gradient: 45-75% (% B)). The desired fractions were collected and the solvent was removed under reduced pressure to afford 77.

Preparation of Intermediate 78

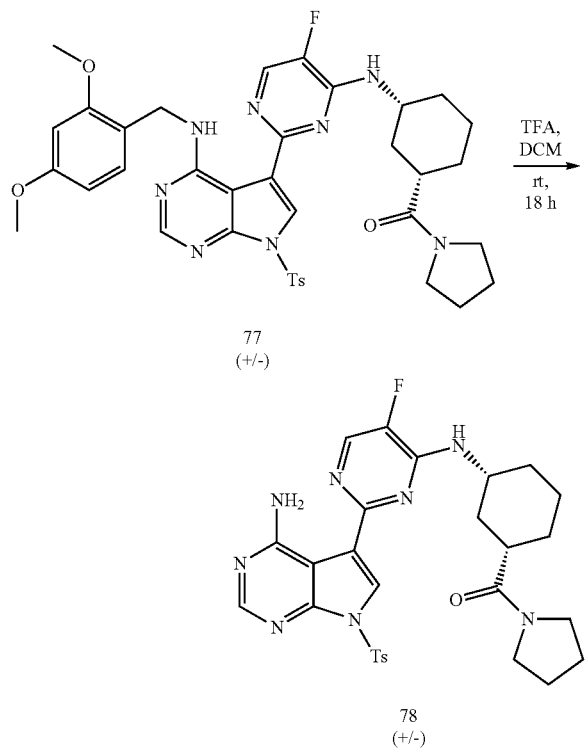

To a solution of 77 (120 mg, 0.161 mmol) in DCM (2 mL) was added TFA (2 mL) and the entire solution was stirred for 16 h at room temperature. The solvent was removed under reduced pressure and the residue containing 78 was directly used for the next step. LC-MS ES⁺ m/z=594.2; Rt: 0.78 min, method E.

Preparation of 79

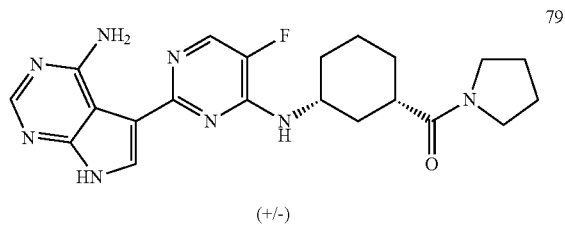 [SMILES: Nc1ncnc2[nH]cc(-c3ncc(F)c(N[C@@H]4CCC[C@H](C(=O)N5CCCC5)C4)n3)c12]

To a flask containing 78 (90 mg, 0.152 mmol) in methanol (5 mL) was added sodium methoxide (33 mg, 0.608 mmol) at room temperature. Then the mixture was stirred at room temperature for 2 h. The mixture was poured into water and extracted three times with EtOAc. The combined organic layers were washed with brine, dried (MgSO₄), and concentrated. The crude mixture was purified by reverse phase Column chromatography: (Agela DuraShell C18 150×25×5 μm, Flow rate: 35 ml/min, Mobile Phase A: water (containing 0.05% NH₃.H₂O), Mobile Phase B: Acetonitrile, Gradient: 26-56% (% B)). The desired fractions were collected and the solvent was removed under reduced pressure, yielding 79. ¹H NMR (400 MHz, chloroform-d) δ ppm 0.97-1.35 (m, 3 H) 1.42-1.68 (m, 2 H) 1.86-1.95 (m, 4 H) 1.96-2.13 (m, 2 H) 2.64-2.76 (m, 1 H) 3.28-3.35 (m, 3 H) 3.83-3.97 (m, 1 H) 4.04-4.12 (m, 1 H) 4.94 (br d, J=7.03 Hz, 1 H) 7.94 (d, J=3.01 Hz, 1 H) 7.98 (s, 1 H) 8.26 (s, 1 H). LC-MS ES⁺ m/z=440.2; Rt: 3.72 min, method E.

Preparation of 80

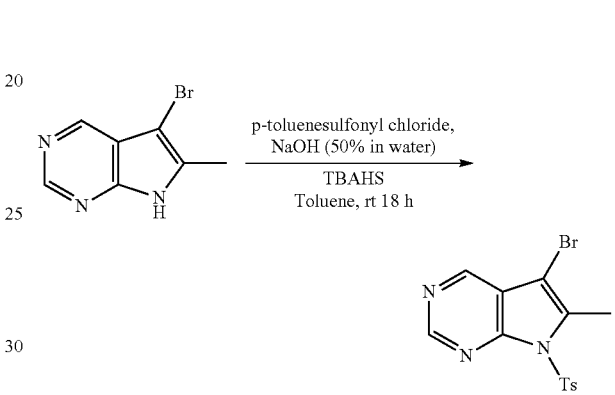

To a solution of 5-bromo-6-methyl-7H-pyrrolo[2,3-d]pyrimidine (300 mg, 1.415 mmol) in toluene (15 mL) was added tetrabutyl ammonium hydrogen sulfate (28.4 mg, 0.113 mmol) followed by NaOH (50% in water) (5 mL) and the mixture was stirred vigorously. A solution of p-toluenesulfonyl chloride (378 mg, 1.98 mmol) in toluene (15 mL) was added and the entire mixture was stirred at room temperature for 18 h. The organic layer was separated and washed with water, dried (MgSO₄) and concentrated. The crude containing 80 was used in the next step without further purification. LC-MS ES⁺ m/z=367; Rt: 1.031 min, method C.

Preparation of 81

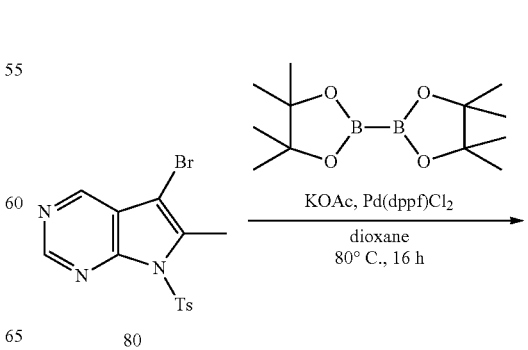

-continued

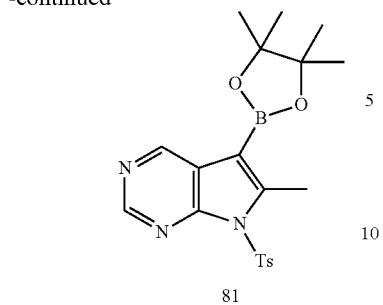

81

Compound 81 was prepared according to the methods to prepare 3. LC-MS ES⁺ m/z=414; Rt: 1.257 min, method C.

Preparation of 82

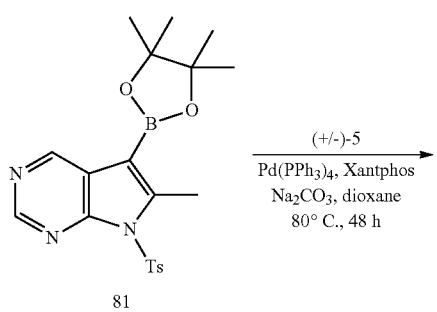

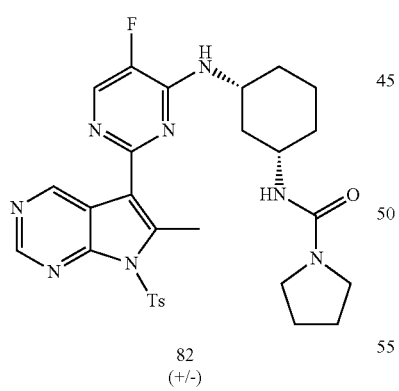

82
(+/−)

A mixture of 98 (100 mg, 0.242 mmol), 5 (107.7 mg, 0.315 mmol), Pd(PPh$_3$)$_4$ (140 mg, 0.121 mmol), Xantphos (70 mg, 0.121 mmol), 2M Na$_2$CO$_3$ (0.363 mL, 2 M, 0.726 mmol), dioxane (10 mL) was stirred at 80° C. for 48 h. The reaction mixture was filtered through a pad of celite and washed with ethyl acetate. The solvents were removed under reduced pressure. The residue containing 82 was directly used for the next step. LC-MS ES⁺ m/z=593; Rt: 1.094 min, method C.

Preparation of 83

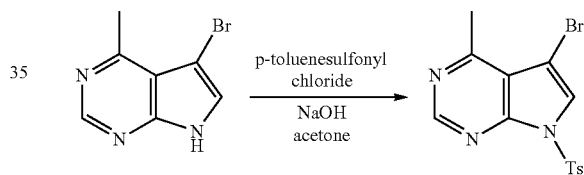

83

(+/−)

Compound 83 was prepared according to the methods to prepare 29. ¹H NMR (300 MHz, DMSO-d$_6$) δ ppm 1.20-1.44 (m, 5 H) 1.72-1.86 (m, 6 H) 1.87-2.06 (m, 1 H) 2.08-2.21 (m, 1 H) 2.86 (s, 2 H) 3.16-3.22 (m, 4 H) 3.50-3.68 (m, 1 H) 3.97-4.13 (m, 1 H) 5.82 (br d, J=7.97 Hz, 1 H) 7.54 (br d, J=7.56 Hz, 1 H) 8.21 (d, J=3.85 Hz, 1 H) 8.73 (s, 1 H) 9.57 (s, 1 H) 12.33 (s, 1 H). LC-MS ES⁺ m/z=439; Rt: 2.160 min, method C.

Preparation of 84

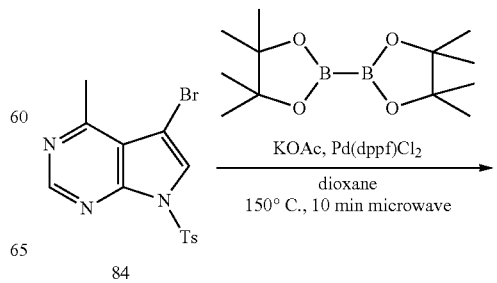

To a solution of 5-bromo-4-methyl-7H-pyrrolo[2,3-d]pyrimidine (2 g, 9.43 mmol) in acetone (20 mL) was added a 2N NaOH solution (9.43 mL, 18.87 mmol), followed by of p-toluenesulfonyl chloride (1.98 g, 10.38 mmol) at 0° C. and the mixture was stirred for 18 h. The reaction mixture was concentrated and the water layer was extracted with EtOAc. The organic layer was separated and washed with water, dried (MgSO$_4$) and concentrated. The residue containing 84 was directly used for the next step.

Preparation of 85

Preparation of 86

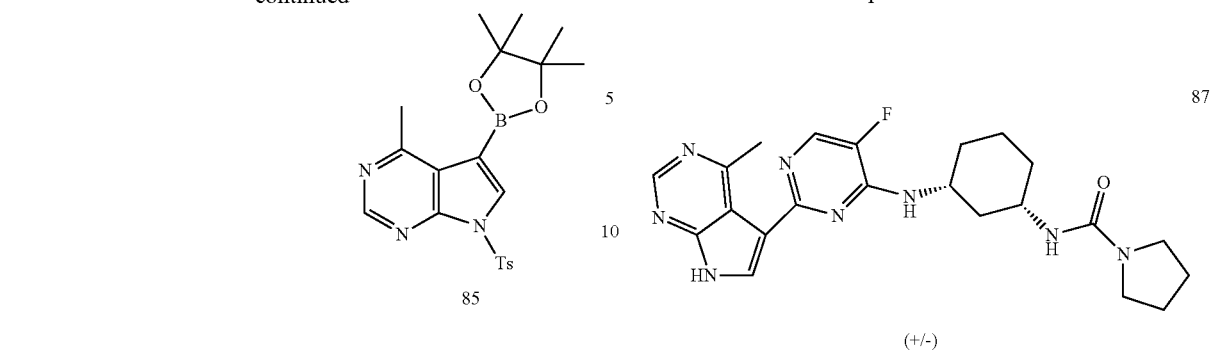

85 was prepared according to the methods to prepare compound 3.

Preparation of 86

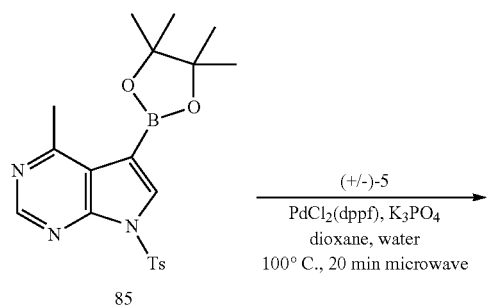

A mixture of 84 (180 mg, 1.47 mmol), 5 (223.5 mg, 0.65 mmol), K$_3$PO$_4$ (278 mg, 1.31 mmol), and [1,1'-bis(di-tert-butylphosphino)ferrocene]dichloropalladium(II) (28.5 mg, 0.04 mmol) in 1,4-dioxane (15 mL) and water (3 mL) was heated to 100° C. for 20 minutes under microwave irradiation. The reaction mixture was filtered over Celite and concentrated. The mixture containing 85 was used directly in the next step.

To a mixture of 86 (180 mg, 0.304 mmol) in methanol (10 mL) was added NaOMe (66 mg, 1.22 mmol) and stirred for two hours at room temperature. The reaction mixture was poured into water and extracted three times with EtOAc. The organic layers were separated and washed with water, dried (Na$_2$SO$_4$) and concentrated. The crude mixture was purified by reverse phase column chromatography. Column: Waters Xbridge C18 150×20 mm×5 µm, Flow rate: 25 mL/min, Mobile Phase A: water (containing 0.05% NH$_3$.H$_2$O), Mobile Phase B: acetonitrile, Gradient: 18-48% (% B). The desired fractions were concentrated to afford 87. $^1$H NMR (400 MHz, chloroform-d) δ ppm 1.09 (br d, J=11.54 Hz, 4 H) 1.51-1.59 (m, 1 H) 1.85-1.94 (m, 6 H) 2.03-2.16 (m, 2 H) 2.60-2.69 (m, 1 H) 3.09 (s, 3 H) 3.27-3.36 (m, 4 H) 3.80-3.92 (m, 1 H) 4.04 (d, J=7.28 Hz, 1 H) 4.12-4.29 (m, 1 H) 4.90 (br d, J=5.52 Hz, 1 H) 8.00 (s, 1 H) 8.09 (d, J=3.01 Hz, 1 H) 8.79 (s, 1 H) 9.87 (s, 1 H). LC-MS ES$^+$ m/z=439.2; Rt: 3.19 min, method E.

Preparation of 88

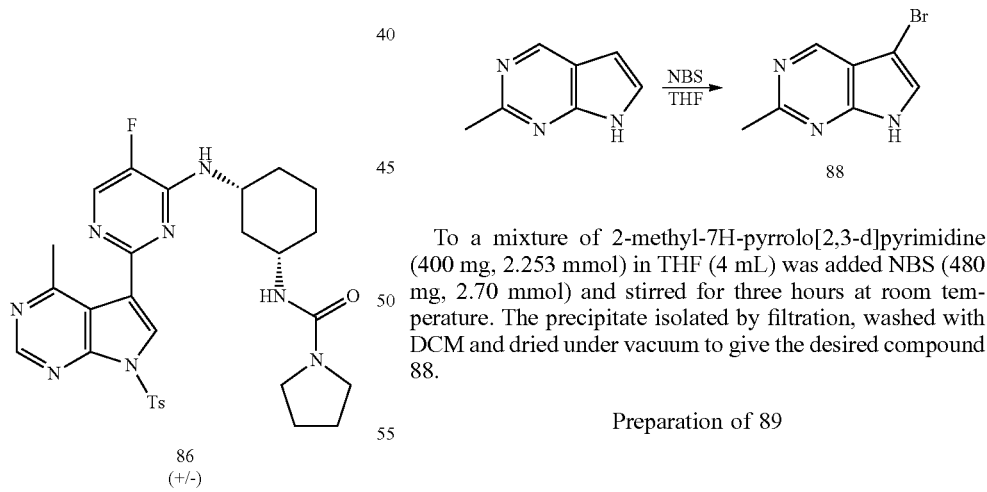

To a mixture of 2-methyl-7H-pyrrolo[2,3-d]pyrimidine (400 mg, 2.253 mmol) in THF (4 mL) was added NBS (480 mg, 2.70 mmol) and stirred for three hours at room temperature. The precipitate isolated by filtration, washed with DCM and dried under vacuum to give the desired compound 88.

Preparation of 89

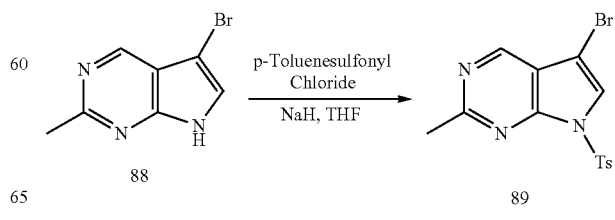

To a stirred solution of 88 (230 mg, 1.085 mmol) in THF (25 mL) was added NaH (80 mg, 2 mmol) portion wise at room temperature under nitrogen. The resulting mixture was stirred at room temperature for 1 hour then p-toluenesulfonyl chloride (264 mg, 1.385 mmol) was added. The reaction mixture was stirred for 3 hours at room temperature. The reaction mixture was concentrated under reduced pressure. The crude reaction mixture was purified by flash column chromatography over silica. (Gradient: petroleum ether/EtOAc (65/35)). The desired fractions were collected and evaporated to dryness, to afford 89.

Preparation of 107

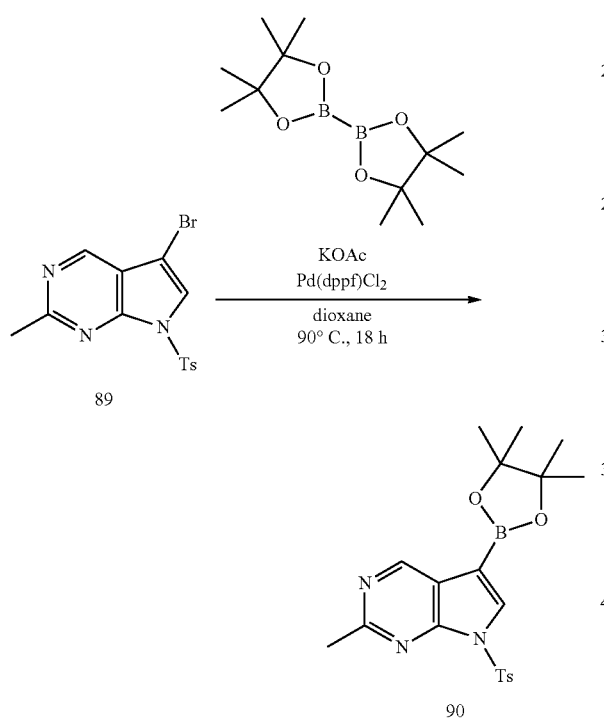

Intermediate 90 was prepared according to the methods to prepare intermediate 3.

Preparation of 91

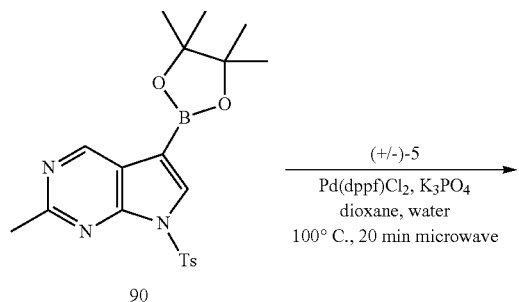

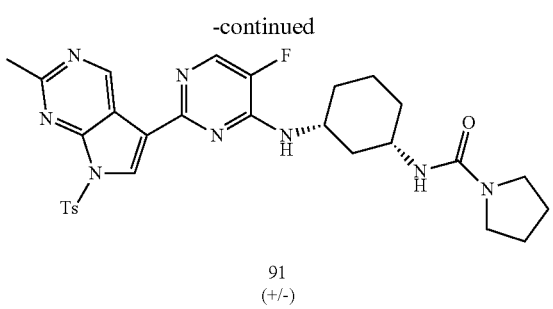

91
(+/−)

A mixture of 90 (165.4 mg, 0.484 mmol), 5 (200 mg, 0.484 mmol), K$_3$PO$_4$ (308 mg, 1.45 mmol), and [1,1'-bis(di-tert-butylphosphino)ferrocene]dichloropalladium(11) (31.5 mg, 0.049 mmol) in 1,4-dioxane (20 mL) and water (5 mL) was heated to 80° C. for 18 h. The reaction mixture was filtered over Celite and concentrated. The mixture containing 91 was used directly for next step.

Preparation of 92

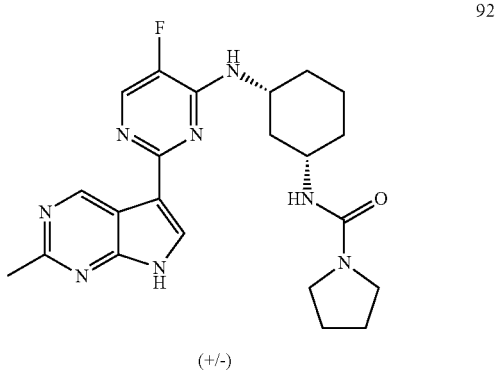 [SMILES: Cc1ncc2c(-c3ncc(F)c(N[C@@H]4CCC[C@H](NC(=O)N5CCCC5)C4)n3)c[nH]c2n1]

92

(+/−)

Compound 92 was prepared according to the method to prepare 104. $^1$H NMR (400 MHz, chloroform-d) δ ppm 1.08-1.29 (m, 4 H) 1.88-1.92 (m, 4 H) 2.08 (m, J=14.10 Hz, 1 H) 2.17-2.25 (m, 1 H) 2.62-2.69 (m, 1 H) 2.77-2.83 (m, 1 H) 2.81 (s, 2 H) 3.25-3.29 (m, 1 H) 3.29-3.34 (m, 3 H) 3.84-3.93 (m, 1 H) 4.04-4.09 (m, 1 H) 4.09-4.18 (m, 1 H) 4.88 (m, 1 H) 8.05-8.08 (m, 2 H) 9.58 (s, 2 H). LC-MS ES$^+$ m/z=439.2; Rt: 3.44 min, method E.

Preparation of 93

Compound 9 was purified via preparatory SFC (Stationary phase: Chiralcel Diacel OD 20×250 mm, Mobile phase: CO$_2$, isopropanol with 0.2% isopropylamine). The desired fractions were collected and the solvent was removed under reduced pressure, yielding 93 $^1$H NMR (400 MHz, methanol-d$_4$) δ ppm 1.22-1.53 (m, 9 H) 1.55-1.67 (m, 1 H) 1.85-1.91 (m, 4 H) 2.13-2.22 (m, 1 H) 2.24-2.32 (m, 1 H) 3.36-3.44 (m, 1 H) 3.70-3.80 (m, 1 H) 4.17-4.27 (m, 1 H) 5.81 (m, 1 H) 7.52 (m, 1 H) 8.39 (s, 1 H) 8.80 (s, 1 H) 9.62 (s, 1 H). LC-MS ES$^+$ m/z=448.2; Rt: 1.55 min, method A.

Preparation of 94

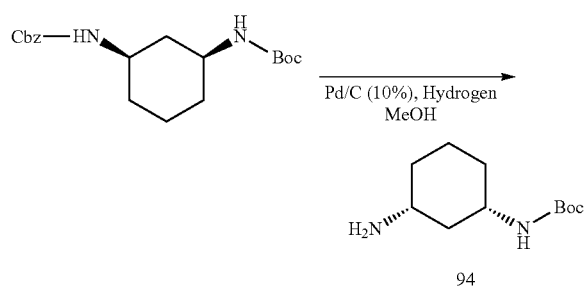

A solution of benzyl tert-butyl (+/−)-cyclohexane-1,3-diyldicarbamate (52.27 g, 150 mmol) in methanol (1.5 L) was stirred under nitrogen atmosphere, Pd/C (10%) (1.6 g, 1.5 mmol) was added and stirring under hydrogen (3.75 L, 0.04 M, 150 mmol) was done overnight at room temperature. The catalyst was filtered off over decalite and under nitrogen, rinsed two times with methanol and the filtrate was evaporated to dryness, yielding 94.

Preparation of 95

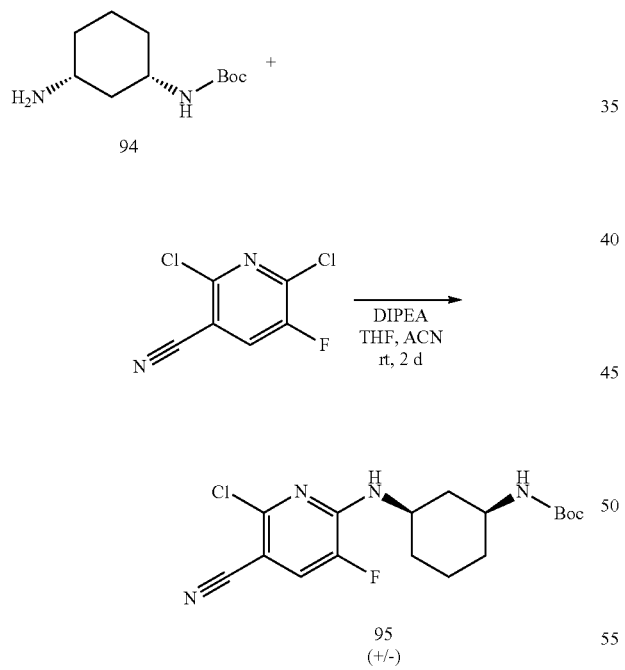

A solution of 2,6-dichloro-5-fluoro-pyridine-3-carbonitrile (19.1 g, 100 mmol) in THF (200 mL) was stirred at room temperature, while a mixture of 94 (12.54 g, 50 mmol) and DIPEA (26 mL, 150 mmol) in ACN (100 mL) was added drop wise. The reaction was allowed to stir over weekend at ambient temperature. The solvent of the mixture was evaporated, the residue was triturated in water and stirred overnight. The precipitate was filtered off and dried in vacuo, yielding 95.

Preparation of 96

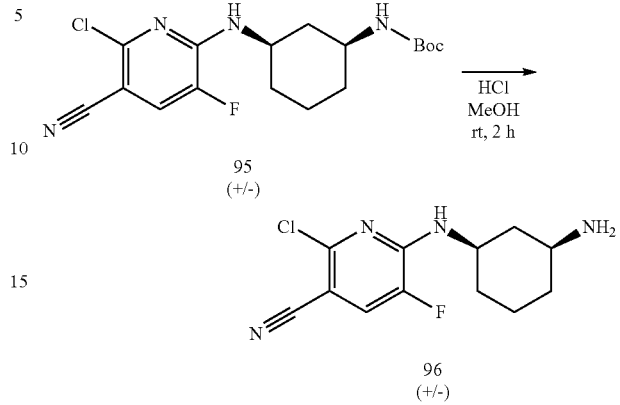

To a solution of HCl (6M in iPrOH) (16.7 mL, 6 M, 100 mmol) in methanol (50 mL), was added 95 (4.61 g, 10 mmol) portion wise and the reaction was stirred for two hours at ambient temperature. The mixture was evaporated to dryness and the residue was triturated in diisopropylether/acetone. The crystals were collected by filtration and dried in vacuo, yielding 96.

Preparation of 97

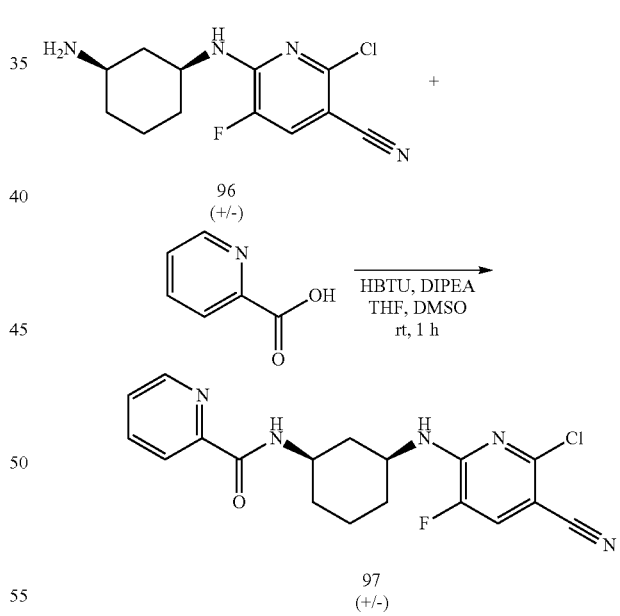

To a flask containing picolinic acid (240.521 mg, 41.954 mmol) in THF (18 mL) was added HBTU (1411 mg, 3.721 mmol) at room temperature. The resulting mixture was stirred for 5 minutes under inert atmosphere. Then a solution of 96 (500 mg, 1.86 mmol) and N,N-Diisopropylethylamine (0.81 mL, 4.652 mmol) in DMSO (1 mL) was added. The mixture was stirred at room temperature for 1 h. Then, the reaction mixture was diluted with water and extracted with ethyl acetate. The organic layers dried (Mg$_2$SO$_4$), filtered, and concentrated under reduced pressure. A purification was performed using a silicagel column (heptane:AcOEt 50:50). The desired fractions were collected and the solvent was removed under reduced pressure, yielding 97. LC-MS ES+ m/z=373.9; Rt: 1.38 min, method C.

Preparation of 155

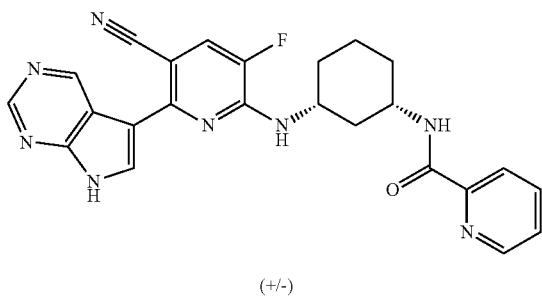

98
(+/-)

A mixture of 3 (200 mg, 0.501 mmol), 97 (187 mg, 0.501 mmol), K$_3$PO$_4$ (33 mg, 0.0501 mmol), and [1,1'-Bis(di-tert-butylphosphino)ferrocene]dichloropalladium(II) (318 mg, 1.503 mmol) in 1,4-dioxane (5 mL) and water (0.5 mL) was heated to 90° C. for 2 h. The reaction mixture was filtered over Celite and concentrated. Then, the reaction mixture was diluted with DCM and washed with water. The organic layer was dried over MgSO$_4$ and purified by reverse phase HPLC (Method: MG3BIC From 70% [Aq. phase]-30% [Organic phase] to 27% [AP]-73% [OP]. AP=25 mM aq. NH$_4$HCO$_3$, OP=acetonitrile:methanol 1:1). The desired fractions were collected and the solvent was removed under reduced pressure to afford 98. LC-MS ES+ m/z=457.2; Rt: 2.39 min, method C.

Preparation of 99

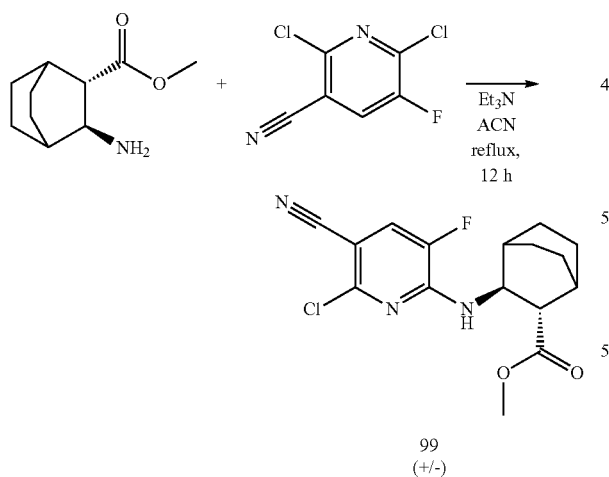

99
(+/-)

A flask containing 2,6-dichloro-5-fluoro-3-pyridinecarbonitrile (1 g, 5.26 mmol), triethylamine (1.61 mL, 11.54 mmol) and (+/−)-methyl 3-aminobyciclo[2.2.2]octane-2-carboxylate (1.04 g, 4.73 mmol) dissolved in ACN (30 mL) was refluxed for 12 hours. The reaction mixture was diluted into EtOAc and brine. The organic phase was dried over MgSO$_4$, filtered and the solvent was concentrated in vacuo. 99 was used in the next step without further purification.

Preparation of 100

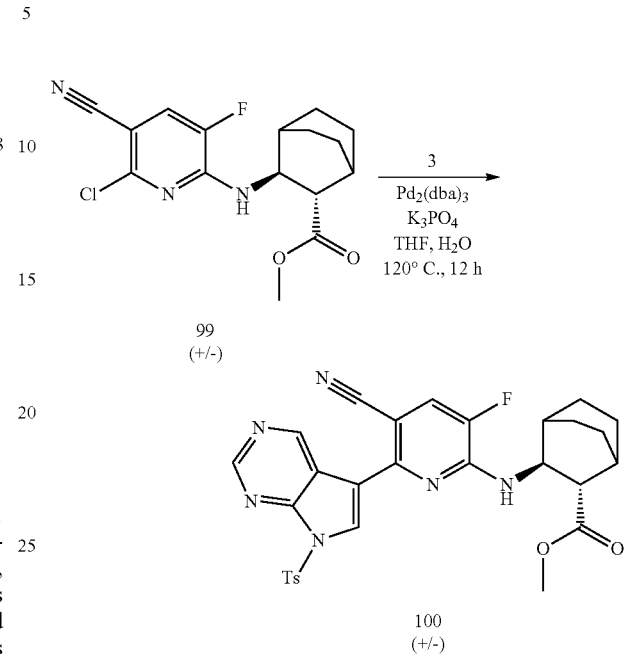

99
(+/-)

100
(+/-)

A solution containing 3 (2.814 g, 7.049 mmol) and 99 (2 g, 54.92 mmol) in THF (40 mL) and water (10 mL) was stirred for 10 min under inert atmosphere at room temperature. Then were added Pd$_2$(dba)$_3$ (0.103 g, 0.141 mmol), tripotassium phosphate (3.753 g, 17.69 mmol), and Xant-Phos (0.336 g, 0.705 mmol) and the mixture was stirred at 120° C. for 12 h. The crude was concentrated under reduced pressure and 100 was used in the next step without further purification.

Preparation of 101

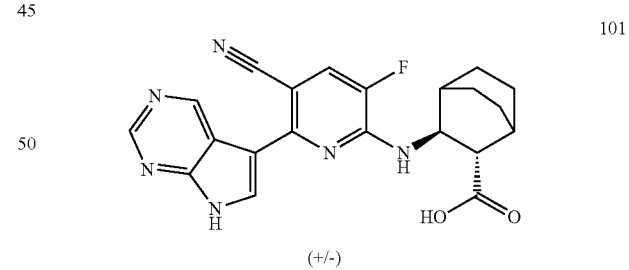

101
(+/-)

To a flask containing 100 (5.103 g, 8.88 mmol) in THF (10 mL) was added sodium methoxide (11.5 mL, 53.28 mmol). The resulting mixture was stirred at 40° C. for 3 hours. Afterwards, the reaction was concentrated under vacuum. The mixture was purified by reverse phase chromatography. (Started: organic phase 19%; Finished: organic phase 55%; organic phase: 0.1% HCOOH:acetonitrile, aq. phase 1:1:25 mM NH$_4$HCO$_3$). The desired fractions were collected and the solvent was removed under reduced pressure, yielding 101. LC-MS ES+ m/z=407; Rt: 2.69 min, method C.

TABLE 1

Compounds of formula (I) and corresponding analytical data.

| Cmpnd # | Structure | ¹H NMR | Rt (min) | LC Method | LC-MS Mass Found [M + H]⁺ |
|---|---|---|---|---|---|
| 29 | 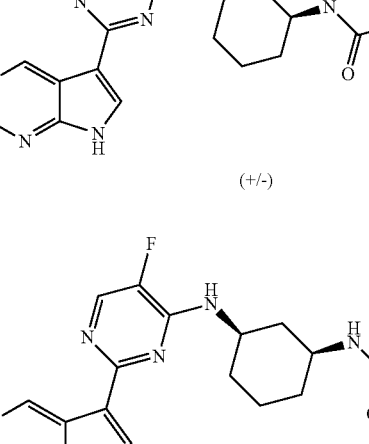 (+/−) | ¹H NMR (300 MHz, DMSO-$d_6$) δ ppm 1.18-2.09 (m, 8 H) 3.99-4.09 (m, 1 H) 4.25 (br s, 1 H) 6.90 (d, J = 1.51 Hz, 1 H) 7.55 (d, J = 7.29 Hz, 1 H) 8.17 (d, J = 3.85 Hz, 1 H) 8.22 (s, 1 H) 8.37 (m, 1 H) 8.80 (s, 1 H) 8.83-8.93 (m, 1 H) 9.25 (m, 1 H) 9.61 (s, 1 H) | 2.16 | C | 473 |
| 30 | 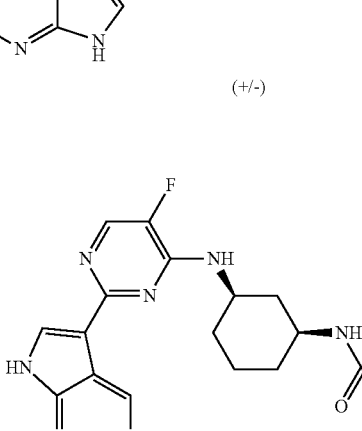 (+/−) | ¹H NMR (300 MHz, DMSO-$d_6$) δ ppm 1.10-1.62 (m, 4 H), 1.75-1.90 (m, 1 H), 1.93-2.04 (m, 1 H), 2.12 (m, 1 H), 2.25 (s, 3 H), 3.75 (s, 3 H), 3.85-4.08 (m, 2 H), 4.20 (br. s., 1 H), 6.39 (s, 1 H), 7.59 (m, 1 H), 7.81 (d, J = 8.1 Hz, 1 H), 8.11-8.24 (m, 2 H), 8.81 (s, 1 H), 9.61 (s, 1 H), 12.51 (br. s., 1 H) | 2.03 | C | 450 |
| 31 | 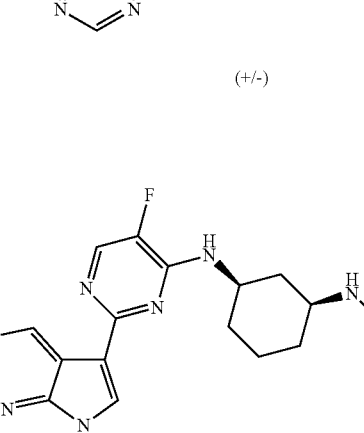 (+/−) | ¹H NMR (300 MHz, methanol-$d_4$) δ ppm 1.13-1.27 (m, 4 H), 1.56 (m, 2 H), 1.83 (br. s., 2 H), 1.96 (m, 1 H), 2.05-2.15 (m, 2 H), 2.31 (br. s., 1 H), 3.70 (br. s., 1 H), 4.20 (br. s., 1 H), 6.76-6.91 (m, 1 H), 7.06-7.16 (m, 2 H), 7.18-7.26 (m, 2 H), 7.93 (m, 1 H), 8.07 (s, 1 H), 8.69 (s, 1 H), 9.59 (s, 1 H) | 2.21 | C | 447 |
| 32 | 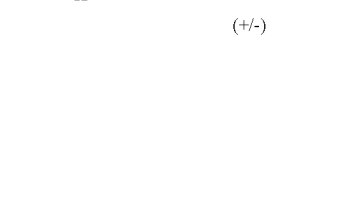 (+/−) | ¹H NMR (300 MHz, methanol-$d_4$) δ ppm 1.18-1.71 (m, 4 H) 1.82-2.03 (m, 2 H) 2.11 (m, 1 H) 2.24 (s, 3 H) 2.35 (m, 1 H) 4.04 (m, 1 H) 4.23 (m, 1 H) 6.71 (s, 1 H) 7.96 (m, 1 H) 8.10 (s, 1 H) 8.71 (s, 1 H) 9.63 (s, 1 H) | 1.99 | C | 437 |

TABLE 1-continued

Compounds of formula (I) and corresponding analytical data.

| Cmpnd # | Structure | ¹H NMR | Rt (min) | LC Method | LC-MS Mass Found [M + H]⁺ |
|---|---|---|---|---|---|
| 33 | 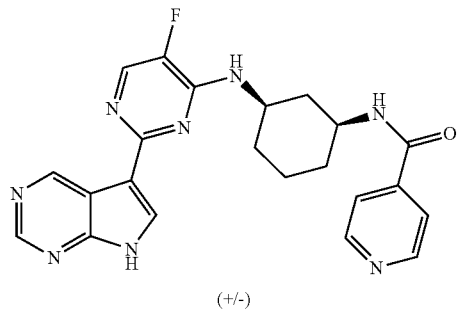 [SMILES: O=C(N[C@H]1CCC[C@@H](Nc2nc(-c3c[nH]c4ncncc34)ncc2F)C1)c1ccncc1] (+/−) | ¹H NMR (300 MHz, DMSO-d$_6$) δ ppm 1.13-1.64 (m, 4 H), 1.78-2.11 (m, 3 H), 2.14-2.31 (m, 1 H), 2.54 (br. s., 1 H), 3.87-4.10 (m, 1 H), 4.23 (br. s., 1 H), 7.61 (m, 1 H), 7.71-7.79 (m, 2 H), 8.18 (m, 1 H), 8.21 (s, 1 H), 8.64 (m, 1 H), 8.68-8.73 (m, 2 H), 8.81 (s, 1 H), 9.62 (s, 1 H) | 1.69 | C | 433 |
| 34 | 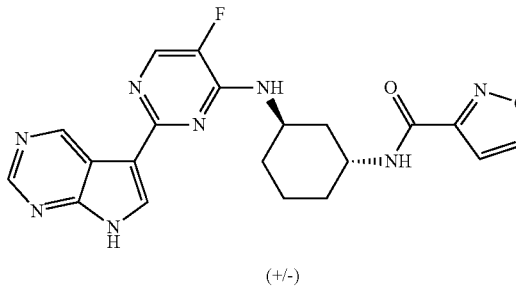 (+/−) | ¹H NMR (300 MHz, methanol-d$_4$) δ ppm 1.16-2.17 (m, 1 H) 1.19-1.46 (m, 3 H) 1.48-1.66 (m, 1 H) 1.84-1.99 (m, 2 H) 2.04-2.14 (m, 1 H) 2.36 (s, 3 H) 4.02 (m, 1 H) 4.22 (br t, J = 11.75 Hz, 1 H) 6.33 (s, 1 H) 7.95 (d, J = 3.99 Hz, 1 H) 8.09 (s, 1 H) 8.70 (s, 1 H) 9.62 (s, 1 H) | 2.05 | C | 437 |
| 35 | 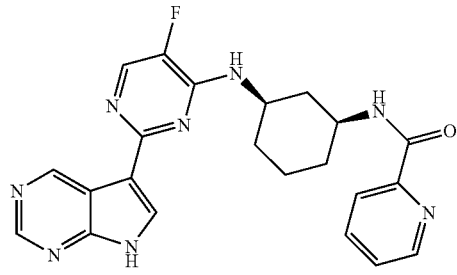 (+/−) | ¹H NMR (300 MHz, methanol-d$_4$) δ ppm 1.24-1.68 (m, 4 H) 1.78-2.05 (m, 2 H) 2.05-2.41 (m, 2 H) 4.00-4.11 (m, 1 H) 4.18-4.31 (m, 1 H) 7.41-7.46 (m, 1 H) 7.84 (m, 1 H) 7.90-8.00 (m, 2 H) 8.09 (s, 1 H) 8.52 (m, 1 H) 8.70 (s, 1 H) 9.61 (s, 1 H) | 2.15 | C | 433 |
| 36 | 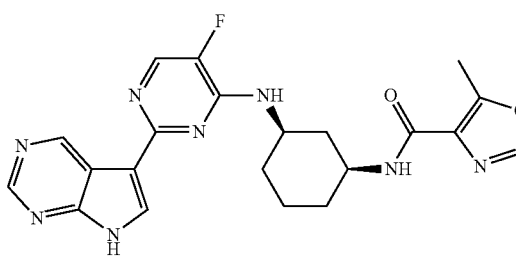 (+/−) | ¹H NMR (300 MHz, DMSO-d$_6$) δ ppm 1.15-1.53 (m, 4 H) 1.67-2.12 (m, 4 H) 2.31 (s, 3 H) 2.43 (s, 6 H) 3.87 (m, 1 H) 4.01-4.21 (m, 1 H) 7.52 (m, 1 H) 7.81 (m, 1 H) 8.07-8.16 (m, 2 H) 8.75 (s, 1 H) 9.55 (s, 1 H) 12.42 (br s, 1 H) | 2.14 | C | 451 |

TABLE 1-continued
Compounds of formula (I) and corresponding analytical data.
| Cmpnd # | Structure | ¹H NMR | Rt (min) | LC Method | LC-MS Mass Found [M + H]⁺ |
|---|---|---|---|---|---|
| 37 | 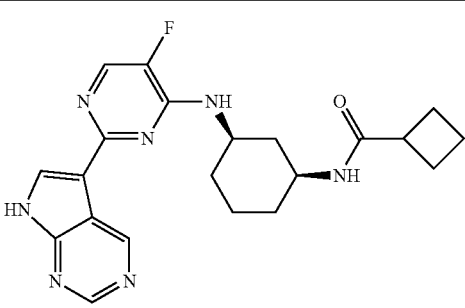 (+/−) | ¹H NMR (300 MHz, chloroform-d) δ ppm 1.21-1.45 (m, 3 H) 1.56 (m, 2 H) 1.74 (m, 1 H) 1.86 (m, 2 H) 2.20 (m, 2 H) 4.09-4.26 (m, 1 H) 5.06 (m, 1 H) 8.08 (m, 1 H) 8.24 (s, 1 H) 8.99 (s, 1 H) 9.81 (s, 1 H) 10.02 (br. s., 1 H) | 2.01 | C | 410 |
| 38 | 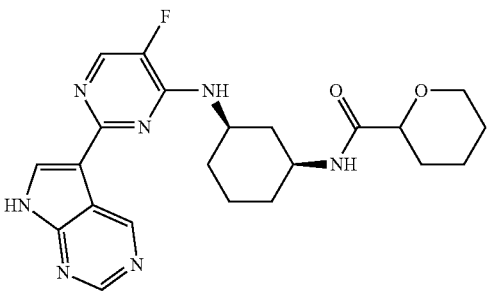 (+/−) | ¹H NMR (300 MHz, DMSO-d₆) δ ppm 1.10-1.28 (m, 4 H), 1.32-1.54 (m, 4 H), 1.71 (m, 4 H), 1.84-2.05 (m, 2 H), 3.32-3.41 (m, 2 H), 3.61 (m, 1 H), 3.72 (m, 1 H), 3.87 (d, J = 11.5 Hz, 1 H), 4.00-4.20 (m, 1 H), 7.37 (d, J = 8.2 Hz, 1 H), 7.50 (d, J = 7.4 Hz, 1 H), 8.05-8.16 (m, 2 H), 8.74 (s, 1 H), 9.53 (s, 1 H) | 2.14 | C | 440 |
| 39 | 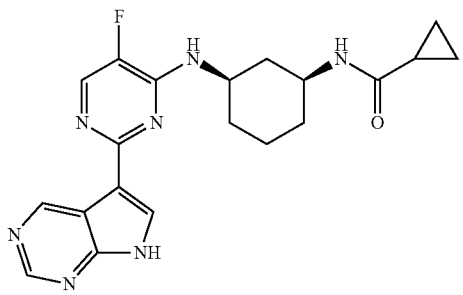 (+/−) | ¹H NMR (300 MHz, chloroform-d) δ ppm 0.60-0.97 (m, 4 H) 1.13-1.23 (m, 4 H) 1.76-2.21 (m, 4 H) 2.56 (s, 1 H) 3.80-3.98 (m, 1 H) 3.98-4.16 (m, 1 H) 4.82 (br d, J = 6.60 Hz, 1 H) 5.50 (br d, J = 8.11 Hz, 1 H) 7.96-8.04 (m, 1 H) 8.06 (s, 1 H) 8.84 (s, 1 H) 9.63 (s, 1 H) | 1.86 | C | 396 |
| 40 | 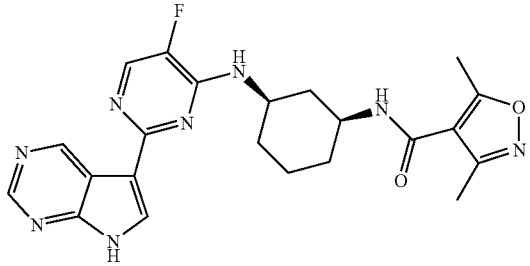 (+/−) |  | 1.99 | C | 451 |

TABLE 1-continued

Compounds of formula (I) and corresponding analytical data.

| Cmpnd # | Structure | ¹H NMR | Rt (min) | LC Method | LC-MS Mass Found [M + H]⁺ |
|---|---|---|---|---|---|
| 41 | (+/−) | | 1.89 | C | 413 |
| 44 | [α]$_D^{20}$ -109.2 (c 0.24, DMF) | ¹H NMR (400 MHz, DMSO-d$_6$) δ ppm 1.27-1.45 (m, 4 H) 1.75 (m, 4 H) 1.78-1.86 (m, 1 H) 1.91-2.01 (m, 1 H) 2.74 (m, 1 H) 4.64 (m, 1 H) 7.42 (m, 1 H) 7.70-7.76 (m, 2 H) 8.82 (s, 1 H) 9.37 (s, 1 H) | 1.58 | B | 449 |
| 45 | (+/−) | ¹H NMR (300 MHz, DMSO-d$_6$) δ ppm 1.27-1.62 (m, 4 H) 1.78-2.05 (m, 3 H) 2.11-2.35 (m, 1 H) 3.80 (s, 3 H) 3.83-4.00 (m, 1 H) 4.09-4.32 (m, 1 H) 5.87-6.15 (m, 1 H) 6.76 (br d, J = 2.34 Hz, 1 H) 6.84 (s, 1 H) 7.59 (br d, J = 7.97 Hz, 1 H) 7.80 (br d, J = 7.97 Hz, 1 H) 7.95-8.43 (m, 2 H) 8.82 (s, 1 H) 9.61 (s, 1 H) 12.52 (br s, 1 H) | 2.20 | C | 435 |
| 47 | (+/−) | ¹H NMR (300 MHz, methanol-d$_4$) δ ppm 1.21-1.70 (m, 4 H) 1.83-2.18 (m, 3 H) 2.29-2.45 (m, 1 H) 3.96-4.13 (m, 1 H) 4.17-4.32 (m, 1 H) 6.84 (m, 1 H) 7.95 (d, J = 3.85 Hz, 1 H) 8.09 (s, 1 H) 8.39 (d, J = 1.79 Hz, 1 H) 8.70 (s, 1 H) 9.63 (s, 1 H) | 1.86 | C | 423 |

TABLE 1-continued

Compounds of formula (I) and corresponding analytical data.

| Cmpnd # | Structure | ¹H NMR | Rt (min) | LC Method | LC-MS Mass Found [M + H]⁺ |
|---|---|---|---|---|---|
| 48 | [α]$_D^{20}$ -121.6 (c 0.19, DMF) | ¹H NMR (400 MHz, DMSO-d$_6$) δ ppm 1.27-1.44 (m, 2 H) 1.54 (m, J = 11.70, 11.70, 11.70 Hz, 2 H) 1.84 (m, J = 11.00 Hz, 2 H) 2.00 (m, J = 12.30 Hz, 1 H) 2.14 (m, J = 11.90 Hz, 1 H) 3.67 (s, 3 H) 3.89-4.04 (m, 1 H) 4.21 (m, J = 7.80, 3.40 Hz, 1 H) 7.53-7.71 (m, 4 H) 8.10-8.26 (m, 2 H) 8.81 (s, 1 H) 9.62 (s, 1 H) 12.47 (br. s., 1 H). | 1.27 | B | 435.2 |
| 49 | (+/-) | ¹H NMR (300 MHz, DMSO-d$_6$) δ ppm 1.25-1.60 (m, 4 H) 1.80-2.07 (m, 3 H) 2.20-2.37 (m, 1 H) 3.93-4.07 (m, 1 H) 4.17-4.31 (m, 1 H) 7.41 (dd, J = 7.84, 4.81 Hz, 1 H) 8.07 (d, J = 3.99 Hz, 1 H) 8.13 (s, 1 H) 8.09-8.17 (m, 1 H) 8.60 (d, J = 4.67 Hz, 1 H) 8.75 (s, 1 H) 8.92 (s, 1 H) 9.60 (s, 1 H) | 1.73 | C | 433 |
| 54 | (+/-) | ¹H NMR (300 MHz, DMSO-d$_6$) δ ppm 0.80-2.10 (m, 8 H) 2.00 (br s, 1 H) 2.28 (s, 1 H) 2.77-2.89 (m, 1 H) 4.63-4.74 (m, 1 H) 6.96-7.52 (m, 1 H) 7.61 (br d, J = 6.60 Hz, 1 H) 8.13 (d, J = 2.34 Hz, 1 H) 8.17 (d, J = 3.99 Hz, 1 H) 8.81 (s, 1 H) 9.67 (s, 1 H) 12.29 (br s, 1 H) 12.47 (br s, 1 H) | 2.29 | C | 383 |
| 55 | (+/-) | ¹H NMR (300 MHz, chloroform-d) δ ppm 1.00 (s, 9 H) 3.09-3.09 (m, 1 H) 3.30-3.38 (m, 1 H) 3.60-3.72 (m, 1 H) 3.91-4.00 (m, 1 H) 4.24-4.24 (m, 1 H) 4.32 (d, J = 3.23 Hz, 1 H) 7.95 (d, J = 3.44 Hz, 1 H) 7.97 (s, 1 H) 8.75 (s, 1 H) 9.66 (br s, 1 H) | 1.87 | C | 331 |

TABLE 1-continued

Compounds of formula (I) and corresponding analytical data.

| Cmpnd # | Structure | ¹H NMR | Rt (min) | LC Method | LC-MS Mass Found [M + H]+ |
|---|---|---|---|---|---|
| 56 | 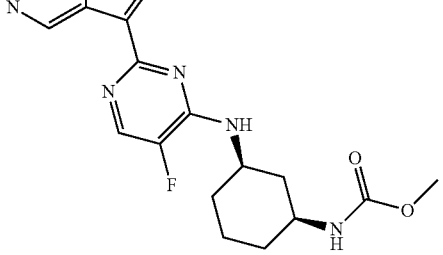 (+/-) | ¹H NMR (300 MHz, DMSO-d$_6$) δ ppm 0.97-1.48 (m, 5 H) 1.68-1.95 (m, 3 H) 2.05 (br d, J = 10.58 Hz, 1 H) 3.44 (s, 3 H) 3.90-4.20 (m, 1 H) 7.11 (br d, J = 7.15 Hz, 1 H) 7.50 (br d, J = 7.56 Hz, 1 H) 8.08-8.14 (m, 2 H) 8.74 (s, 1 H) 9.53 (s, 1 H) 12.42 (br s, 1 H) | 1.84 | C | 386 |
| 57 | 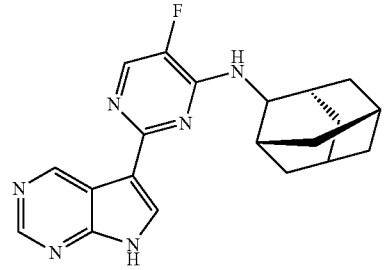 (+/-) | ¹H NMR (300 MHz, methanol-d$_4$) δ ppm 1.16-2.35 (m, 14 H) 4.35 (br s, 1 H) 7.96 (d, J = 3.99 Hz, 1 H) 8.04 (s, 1 H) 8.69 (s, 1 H) 9.59 (s, 1 H) | 3.09 | C | 365 |
| 58 | 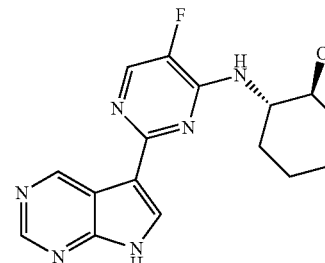 (+/-) | ¹H NMR (300 MHz, DMSO-d$_6$) δ ppm 1.16-1.44 (m, 4 H) 1.61-1.84 (m, 2 H) 1.93-2.14 (m, 2 H) 3.49-3.63 (m, 1 H) 3.90-4.07 (m, 1 H) 4.70 (m, 1 H) 7.36 (m, 1 H) 8.16 (s, 2 H) 8.82 (s, 1 H) 9.65 (s, 1 H) 12.46 (br s, 1 H) | 1.67 | C | 329 |
| 62 | 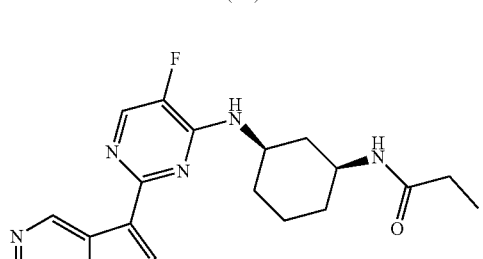 (+/-) | ¹H NMR (300 MHz, DMSO-d$_6$) δ ppm 0.91 (t, J = 7.56 Hz, 3 H) 1.02-1.42 (m, 4 H) 1.68-1.81 (m, 2 H) 1.86-2.07 (m, 4 H) 3.59-3.73 (m, 1 H) 4.03-4.17 (m, 1 H) 7.48 (br d, J = 7.70 Hz, 1 H) 7.65 (br d, J = 7.70 Hz, 1 H) 8.08-8.13 (m, 2 H) 8.74 (s, 1 H) 9.53 (s, 1 H) 12.40 (br s, 1 H) | 1.70 | C | 384 |

TABLE 1-continued
Compounds of formula (I) and corresponding analytical data.
| Cmpnd # | Structure | ¹H NMR | Rt (min) | LC Method | LC-MS Mass Found [M + H]⁺ |
|---|---|---|---|---|---|
| 63 | 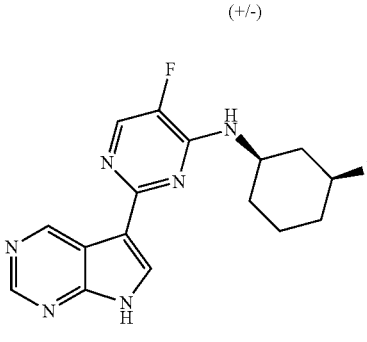 (+/-) | ¹H NMR (300 MHz, DMSO-d₆) δ ppm 0.98-1.54 (m, 4 H) 1.66-2.00 (m, 3 H) 2.07-2.23 (m, 1 H) 3.82 (br d, J = 9.07 Hz, 1 H) 4.16 (br d, J = 7.01 Hz, 1 H) 7.27-7.35 (m, 2 H) 7.43-7.56 (m, 2 H) 8.10 (d, J = 3.85 Hz, 1 H) 8.12-8.15 (m, 1 H) 8.74 (s, 1 H) 9.55 (s, 1 H) | 1.89 | C | 476 |
| 64 | 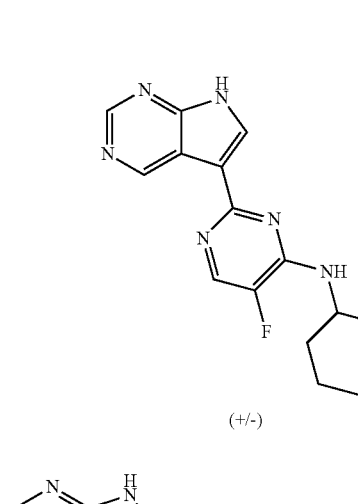 (+/-) | ¹H NMR (300 MHz, DMSO-d₆) δ ppm 1.08 (s, 9 H) 1.19-1.53 (m, 5 H) 1.69-1.88 (m, 2 H) 1.94-2.10 (m, 2 H) 3.70-3.85 (m, 1 H) 4.12-4.25 (m, 1 H) 7.24 (br d, J = 7.84 Hz, 1 H) 7.65 (br d, J = 7.70 Hz, 1 H) 8.20 (d, J = 3.96 Hz, 1 H) 8.24-8.28 (m, 1 H) 8.88 (s, 1 H) 9.62 (s, 1 H) 12.67 (br s, 1 H) | 2.14 | C | 412 |
| 65 | 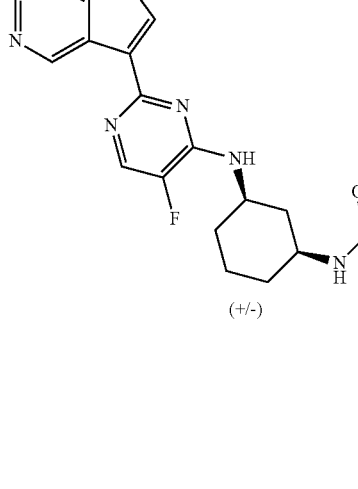 (+/-) | ¹H NMR (300 MHz, chloroform-d) δ ppm 1.14-1.38 (m, 3 H) 1.39-1.57 (m, 2 H) 1.58-1.72 (m, 1 H) 1.72-1.85 (m, 2 H) 2.06-2.21 (m, 2 H) 4.01-4.20 (m, 1 H) 4.98 (br s, 1 H) 8.00 (s, 1 H) 8.16 (s, 1 H) 8.91 (s, 1 H) 9.73 (s, 1 H) | 2.28 | C | 313 |
| 66 | 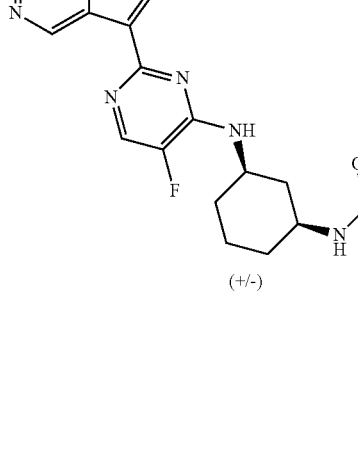 (+/-) |  | 1.71 | C | 400 |

TABLE 1-continued

Compounds of formula (I) and corresponding analytical data.

| Cmpnd # | Structure | ¹H NMR | Rt (min) | LC Method | LC-MS Mass Found [M + H]⁺ |
|---|---|---|---|---|---|
| 73 | (+/−) | ¹H NMR (300 MHz, chloroform-d) δ ppm 1.05-1.12 (m, 5 H) 1.17-1.44 (m, 4 H) 1.62 (m, 1 H) 1.80-2.01 (m, 2 H) 2.10-2.25 (m, 1 H) 2.28-2.47 (m, 2 H) 3.28-3.33 (m, 2 H) 3.81-3.93 (m, 1 H) 4.18-4.30 (m, 1 H) 8.00 (d, J = 3.99 Hz, 1 H) 8.13 (s, 1 H) 8.77 (s, 1 H) 9.66 (s, 1 H) | 1.87 | C | 398 |
| 93 | (+/−) | ¹H NMR (400 MHz, methanol-d₄) δ ppm 1.22-1.53 (m, 9 H) 1.55-1.67 (m, 1 H) 1.85-1.91 (m, 4 H) 2.13-2.22 (m, 1 H) 2.24-2.32 (m, 1 H) 3.36-3.44 (m, 1 H) 3.70-3.80 (m, 1 H) 4.17-4.27 (m, 1 H) 5.81 (d, J = 7.70 Hz, 1 H) 7.52 (d, J = 11.00 Hz, 1 H) 8.39 (s, 1 H) 8.80 (s, 1 H) 9.62 (s, 1 H) | 1.55 | B | 448.2 |

Compounds were prepared according to methods described in the experimental section.
Rt = retention time.

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the mass spectrometer (MS) which was configured with an atmospheric pressure ion source. It is within the knowledge of the skilled person to set the tune parameters (e.g. scanning range, dwell time, etc.) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the [M+H]⁺ (protonated molecule) and/or [M−H]⁻ (deprotonated molecule). In case the compound was not directly ionizable the type of adduct is specified (i.e. [M+NH₄]⁺, [M+HCOO]⁻, etc.). For molecules with multiple isotopic patterns (Br, Cl, etc), the reported value is the one obtained for the lowest isotope mass. All results were obtained with experimental uncertainties that are commonly associated with the method used.

| Method code | Instrument | Column | Mobile phase | Gradient | Flow Column T (° C.) | Run time (min) |
|---|---|---|---|---|---|---|
| A | Waters: Acquity ® UPLC ®-DAD and SQD | Waters: BEH C18 (1.7 μm, 2.1 × 50 mm) | A: 10 mM CH₃COONH₄ in 95% H₂O + 5% CH₃CN B: CH₃CN | From 95% A to 5% A in 1.3 min, held for 0.7 min. | 0.8 55 | 2 |
| B | Waters: Acquity ® UPLC ®-DAD and SQD | Waters: HSS T3 (1.8 μm, 2.1 × 100 mm) | A: 10 mM CH₃COONH₄ in 95% H₂O + 5% CH₃CN | From 100% A to 5% A in 2.10 min, | 0.7 55 | 3.5 |

-continued

| Method code | Instrument | Column | Mobile phase | Gradient | Flow Column T (° C.) | Run time (min) |
|---|---|---|---|---|---|---|
| | | | B: $CH_3CN$ | to 0% A in 0.90 min, to 5% A in 0.5 min | | |
| C | Agilent 1100-DAD-MSD G1956A | YMC-pack ODS-AQ C18 (50 × 4.6 mm, 3 μm) | A: 0.1% HCOOH in $H_2O$ B: $CH_3CN$ | From 95% A to 5% A in 4.8 min, held for 1.0 min, to 95% A in 0.2 min. | 2.6 35 | 6.0 |
| D | Shimadzu: LCMS2010 | Phenomenex ®: Synergy ™ (2.5 μm, 2.0 × 30 mm) | A: $CF_3COOH$ 0.1% in water, B: $CF_3COOH$ 0.05% in $CH_3CN$ | 90% A for 0.01 min, to 20% A in 0.89 min, to 0% A in 0.6 min, back to 90% A in 0.05 min. | 0.9 60 | 2 |
| E | Agilent: 1100/1200-DAD and MSD | Agilent: TC-C18 (5 μm, 2.1 × 50 mm) | A: CF3COOH 0.1% in water, B: CF3COOH 0.05% in CH3CN | 100% A for 1 min, to 40% A in 4 min, to 15% A in 2.5 min, back to 100% A in 2 min. | 0.8 50 | 10.5 |

"SQD" Single Quadrupole Detector,
"RT" room temperature,
"BEH" bridged ethylsiloxane/silica hybrid,
"HSS" High Strength Silica,
"DAD" Diode Array Detector.
Flow expressed in mL/min;
column temperature (T) in ° C.;
Run time in minutes.

Biological Activity of Compounds of Formula (I)

The in vitro antiviral activity of the compounds was determined using a cell-based antiviral assay. In this assay, the cytopathic effect (CPE) in Madin-Darby Canine Kidney (MDCK) cells infected by influenza virus A/Taiwan/1/86 (H1N1) was monitored in the presence or absence of the compounds. White 384-well microtiter assay plates (Greiner) were filled via acoustic drop ejection using the echo liquid handler (Labcyte, Sunnyvale, Calif.). Two hundred nanoliter of compound stock solutions (100% DMSO) were transferred to the assay plates. MDCK cells were dispensed to the plate at final density of 25,000 or 6,000 cells/well. Then Influenza A/Taiwan/1/86 (H1N1) virus was added at a multiplicity of infection of 0.001 or 0.01, respectively. The wells contain 0.5% DMSO per volume. Virus- and mock-infected controls were included in each test. The plates were incubated at 37° C. in 5% $CO_2$. Three days post-virus exposure, the cytopathic effect was quantified by measuring the reduction in ATP levels using the ATPlite™ kit (PerkinElmer, Zaventem, Belgium) according to the manufacturer's instructions. The $IC_{50}$ was defined as the 50% inhibitory concentration. In parallel, compounds were incubated for three days in white 384-well microtiter plates and the in vitro cytotoxicity of compounds in MDCK cells was determined by measuring the ATP content of the cells using the ATPlite™ kit (PerkinElmer, Zaventem, Belgium) according to the manufacturer's instructions. Cytotoxicity was reported as $CC_{50}$, the concentration that causes a 50% reduction in cell viability.

TABLE 2

Biological Activity of compounds of formula (I).

| Compound # | Influenza A/Taiwan/1/86 $IC_{50}$ μM | TOX MDCK $CC_{50}$ μM |
|---|---|---|
| 7 | 0.005 | >25 |
| 9 | 0.009 | 8.74 |
| 12 | 0.030 | >25 |
| 14 | 0.047 | >25 |
| 16 | 0.036 | >25 |
| 18 | 0.044 | 2.48 |
| 21 | 0.106 | 13.4 |
| 23 | 0.033 | >25 |
| 24 | 0.325 | >25 |
| 28 | 0.351 | >25 |
| 29 | 0.010 | >25 |
| 30 | 0.021 | >25 |
| 31 | 0.021 | >25 |
| 32 | 0.035 | >25 |
| 33 | 0.042 | >100 |
| 34 | 0.040 | >25 |
| 35 | 0.002 | >25 |
| 36 | 0.040 | >25 |
| 37 | 0.205 | >25 |
| 38 | 0.380 | >25 |
| 39 | 0.114 | >25 |
| 40 | 0.190 | >25 |
| 41 | 0.319 | >25 |
| 44 | 0.003 | 9.4 |
| 45 | 0.004 | >25 |
| 46 | 0.005 | >25 |
| 47 | 0.011 | >25 |
| 48 | 0.035 | >25 |
| 49 | 0.046 | >25 |

TABLE 2-continued

Biological Activity of compounds of formula (I).

| Compound # | Influenza A/Taiwan/1/86 IC$_{50}$ µM | TOX MDCK CC$_{50}$ µM |
|---|---|---|
| 53 | 0.65 | >25 |
| 54 | 0.46 | >25 |
| 55 | 0.55 | >25 |
| 56 | 0.60 | >25 |
| 57 | 0.66 | 5.2 |
| 58 | 0.63 | >100 |
| 61 | 0.63 | >25 |
| 62 | 0.70 | >25 |
| 63 | 0.72 | >25 |
| 64 | 0.76 | >25 |
| 65 | 0.81 | 11.6 |
| 66 | 0.82 | >25 |
| 69 | 0.83 | >25 |
| 72 | 0.86 | 10.3 |
| 73 | 0.93 | >25 |
| 79 | 0.15 | >25 |
| 83 | 0.71 | >25 |
| 87 | 0.47 | >25 |
| 92 | 0.18 | >25 |
| 93 | 0.006 | >25 |
| 98 | 0.002 | >25 |
| 101 | 0.036 | 10.5 |

The invention claimed is:

1. A compound of formula (I)

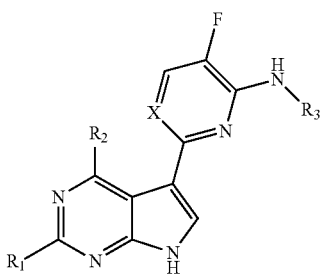

(I)

or a stereoisomeric form, a pharmaceutically acceptable salt, or solvate thereof, wherein X is N or C optionally substituted by a substituent selected from the group consisting of —CN, —CF$_3$, —C$_{1-3}$ alkyl-N—C(O)—C$_{1-3}$ alkyl, —C(O)—NH$_2$, —C(O)—NH—C$_{1-3}$ alkyl, —C(O)N-(dialkyl) and —CH$_2$—NC(O)—CH$_3$;

R$_1$ is H or CH$_3$;

R$_2$ is H or NH$_2$;

R$_3$ is selected from the group consisting of

C$_{1-8}$ alkyl substituted by carboxylic acid;

C$_{3-8}$ cycloalkyl substituted by carboxylic acid, —N—C$_{1-3}$ alkylsulfone, or —N—C(O)—C$_{3-6}$ heterocyclyl optionally substituted by C$_{1-6}$ alkyl; and C$_{3-6}$ heterocyclyl substituted by —N—C(O)—C$_{3-6}$ heterocyclyl.

2. A compound according to claim 1, wherein R$_1$ and R$_2$ are both H.

3. A compound according to claim 1 having the structural formula

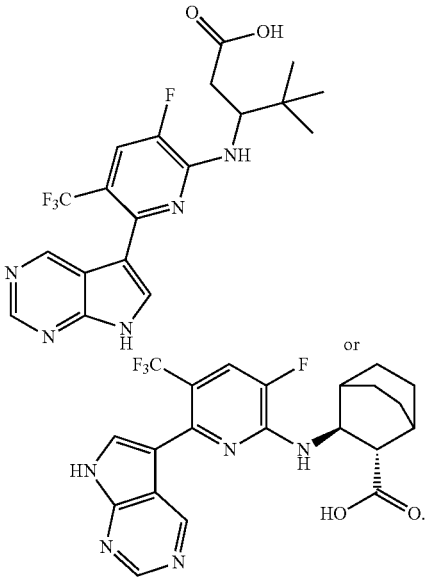

4. A pharmaceutical composition comprising a compound of claim 1, together with one or more pharmaceutically acceptable excipients, diluents or carriers.

5. A method of treating influenza in a subject in need thereof, comprising administering to said subject a therapeutically effective amount of at least one compound of claim 1.

6. A method of treating influenza in a subject in need thereof, comprising administering to said subject a therapeutically effective amount of the pharmaceutical composition according to claim 4.

7. The compound of claim 1,
wherein
X is C substituted by CF$_3$;
R$_1$ is H;
R$_2$ is H;
R$_3$ is C$_{1-8}$ alkyl substituted by carboxylic acid or C$_{3-8}$ cycloalkyl substituted by carboxylic acid.

8. The method of claim 5, further comprising co-administering to said subject an additional therapeutic agent.

9. The method of claim 8, wherein the additional therapeutic agent is at least one of an antiviral agent or influenza vaccine.

10. The compound of claim 1, wherein X is N.

11. The compound of claim 1, wherein X is C substituted by —CN or —CF$_3$.

12. The compound of claim 1, wherein R$_3$ is C$_{1-8}$alkyl substituted by carboxylic acid.

13. The compound of claim 1, wherein R$_3$ is C$_{3-8}$ cycloalkyl substituted by carboxylic acid, —N—C$_{1-3}$ alkylsulfone, or —N—C(O)—C$_{3-6}$ heterocyclyl optionally substituted by C$_{1-6}$ alkyl.

14. The compound of claim 13, wherein R$_3$ is C$_6$cycloalkyl substituted by carboxylic acid, —N—C$_{1-3}$ alkylsulfone, or —N—C(O)—C$_{3-6}$ heterocyclyl optionally substituted by C$_{1-6}$ alkyl.

15. The compound of claim 14, wherein R$_3$ is C$_6$cycloalkyl substituted by —N—C(O)—C$_{3-6}$heterocyclyl optionally substituted by C$_{1-6}$ alkyl.

16. The compound of claim 1, wherein R$_3$ is C$_{3-6}$ heterocyclyl substituted by —N—C(O)—C$_{3-6}$ heterocyclyl.

17. The compound according to claim 1, wherein said compound is selected from the group consisting of
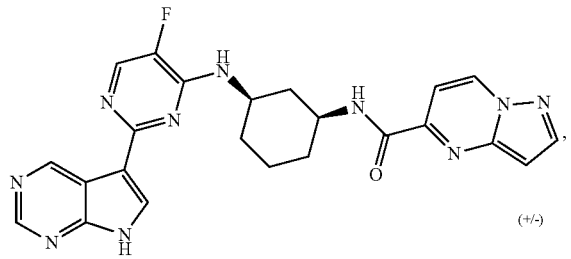
(+/-)
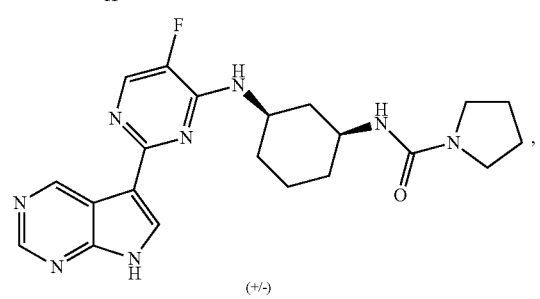
(+/-)
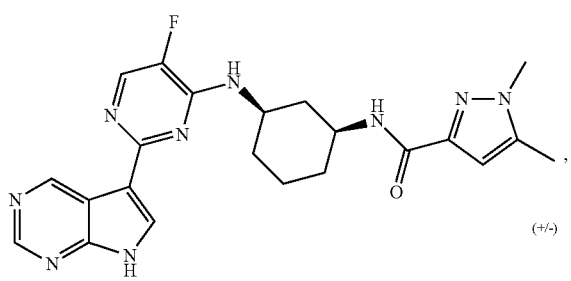
(+/-)
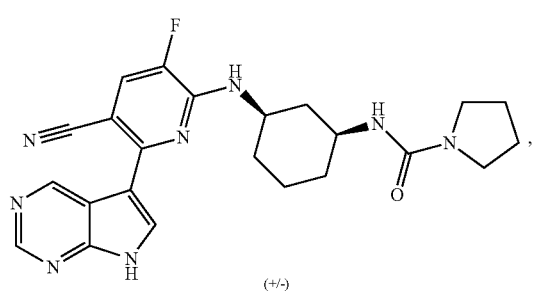
(+/-)
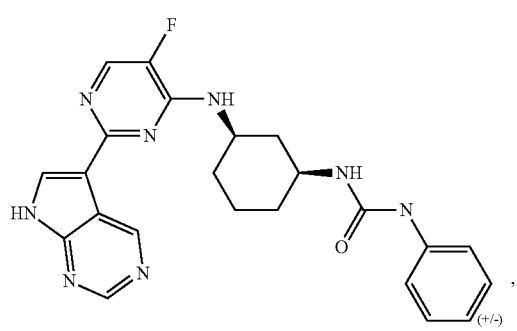
(+/-)
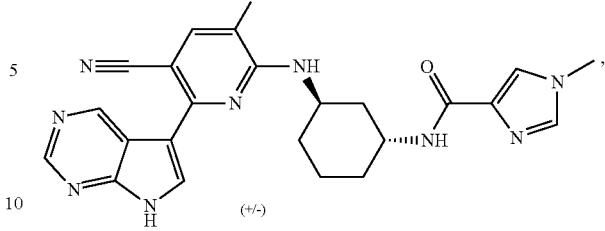
(+/-)
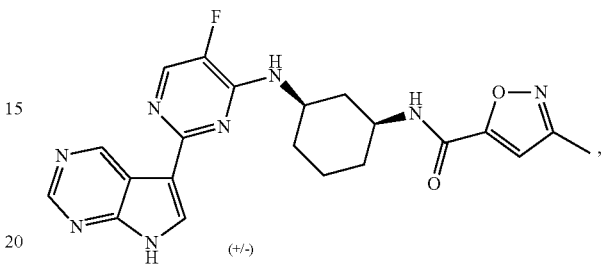
(+/-)
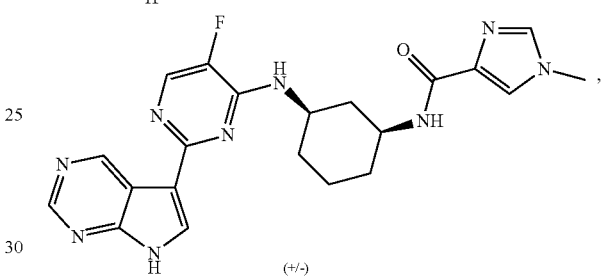
(+/-)
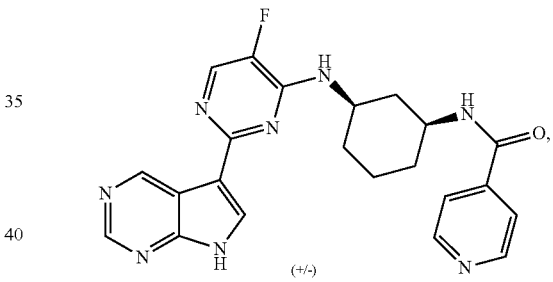
(+/-)
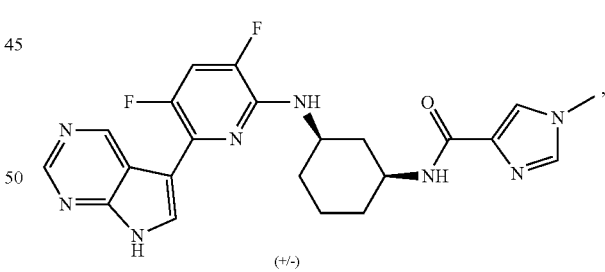
(+/-)
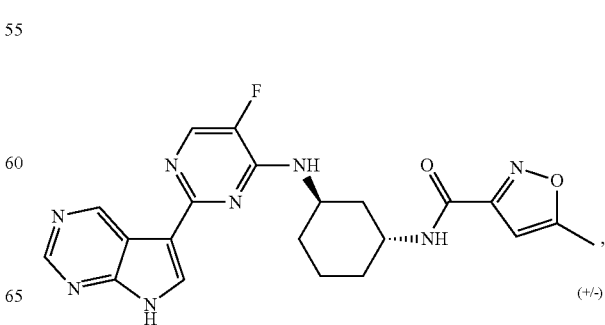
(+/-)

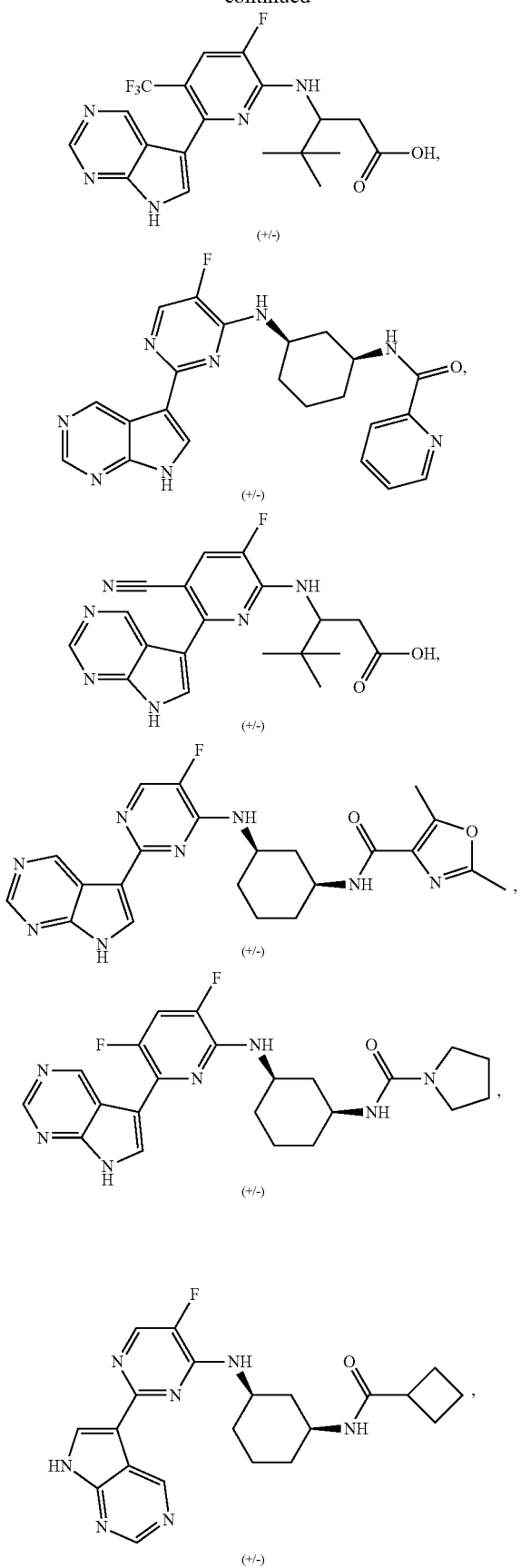
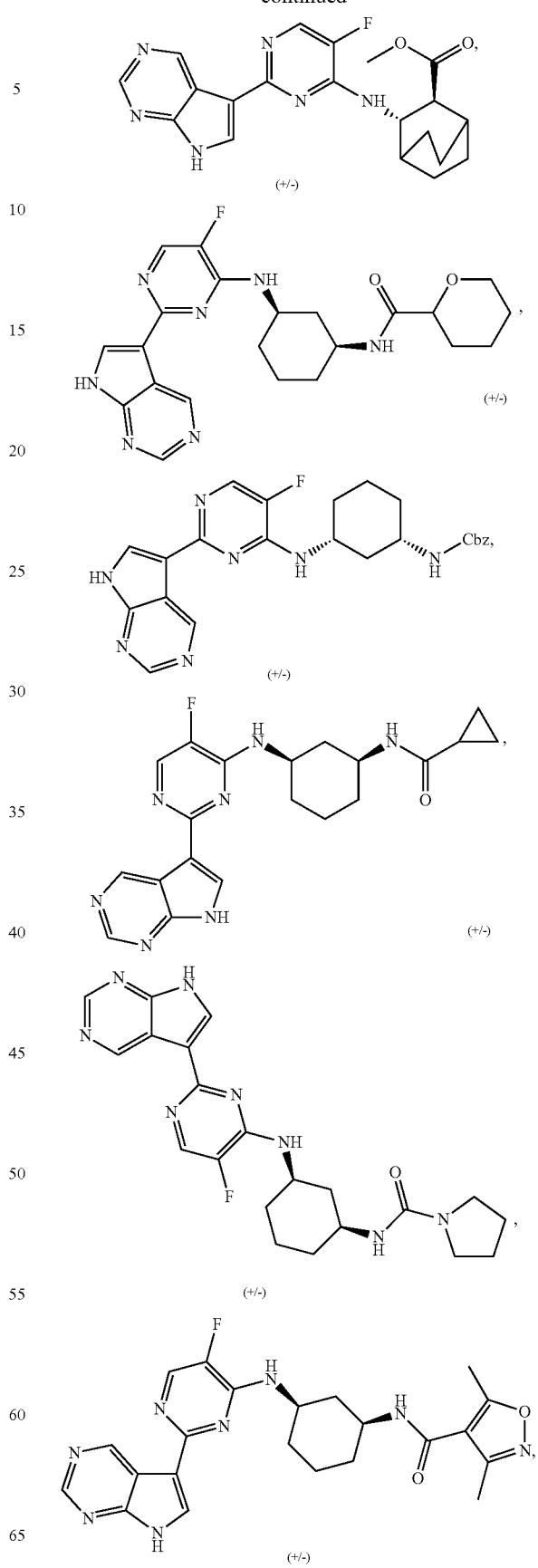

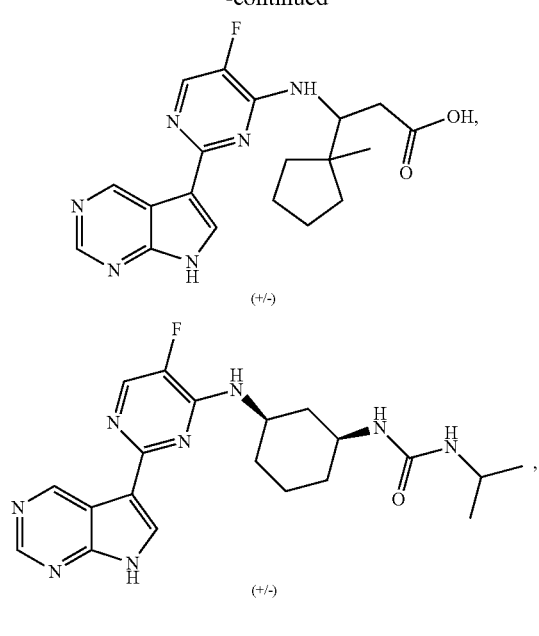
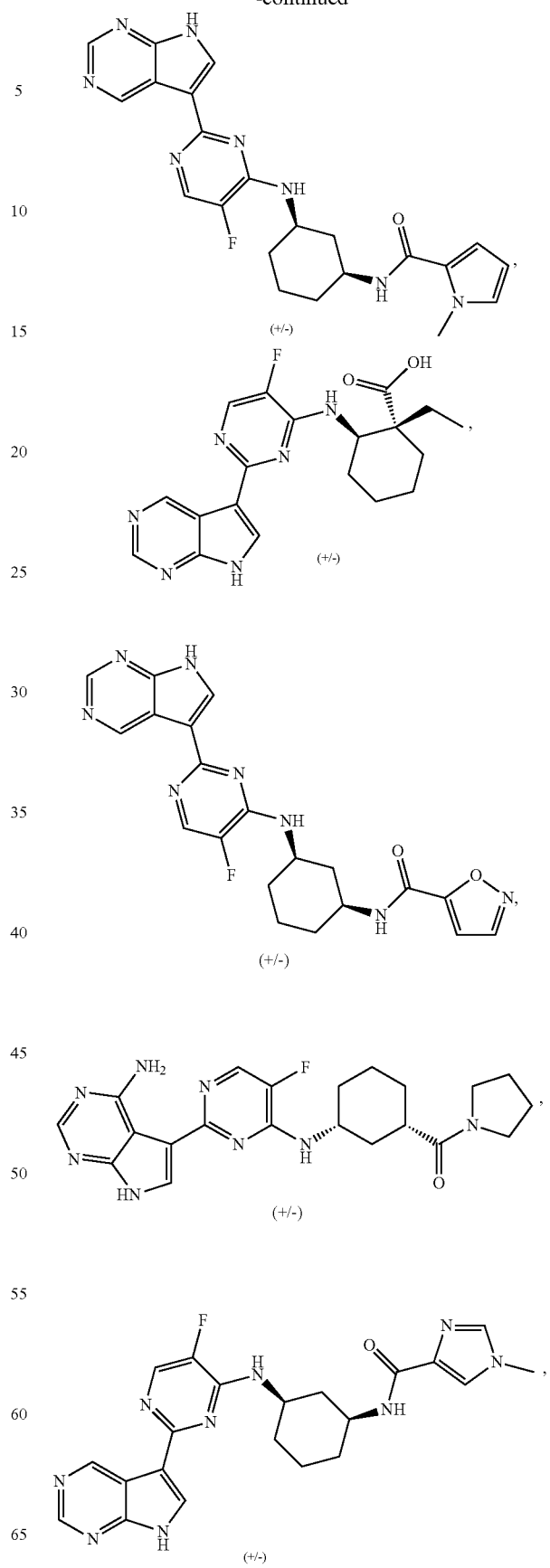

77
-continued
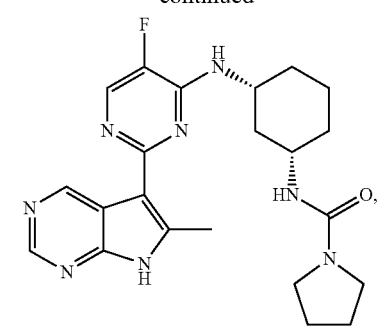
(+/-)
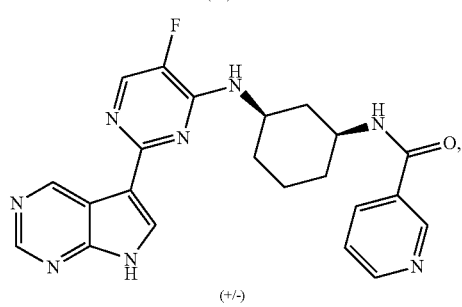
(+/-)
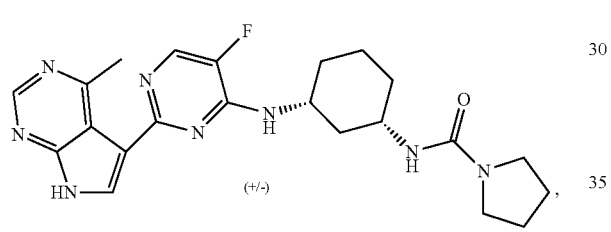
(+/-)
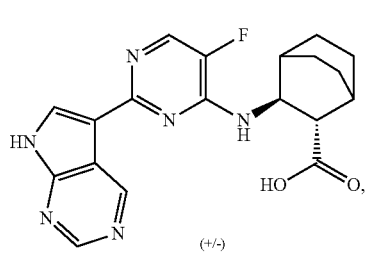
(+/-)
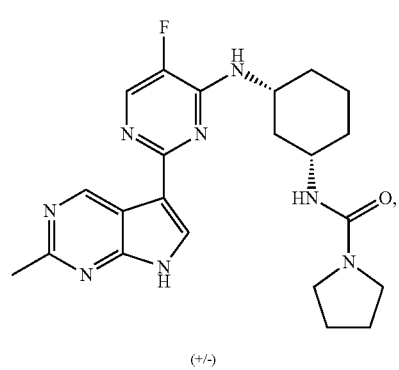
(+/-)
78
-continued
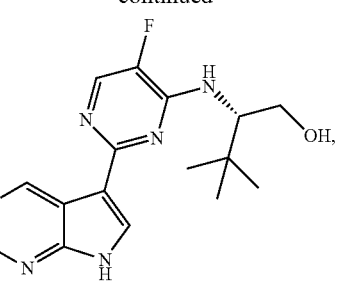
(+/-)
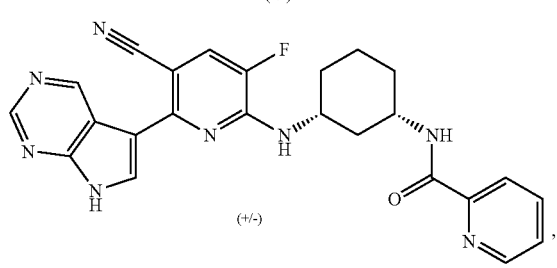
(+/-)
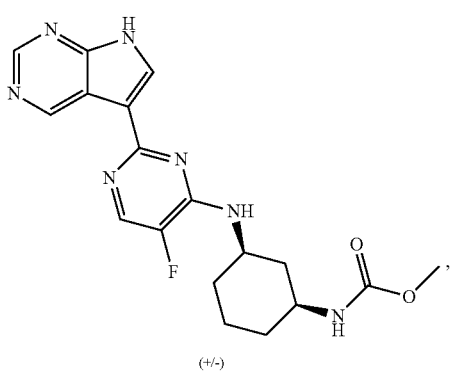
(+/-)
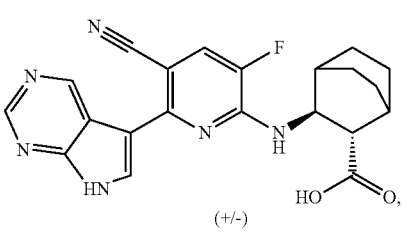
(+/-)
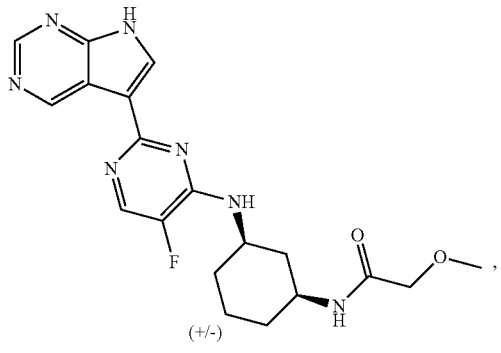
(+/-)

-continued

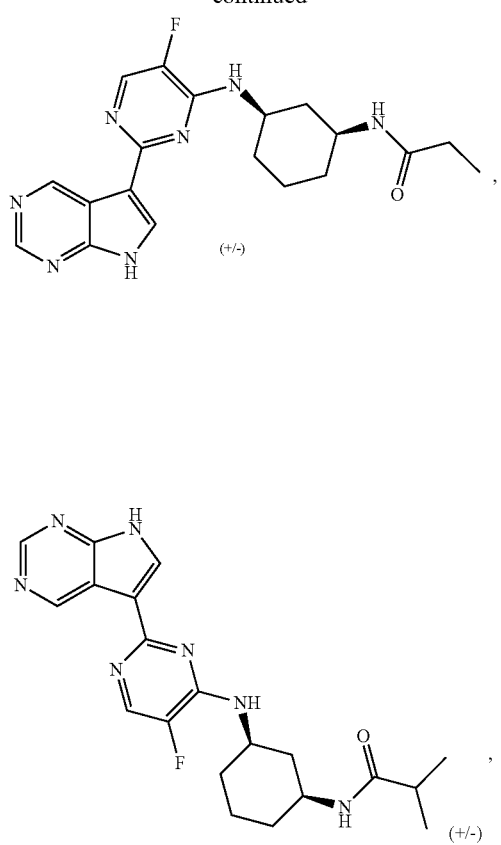

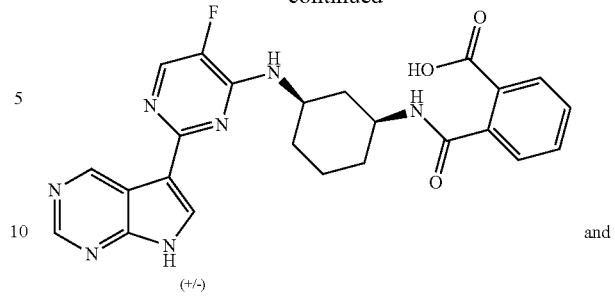

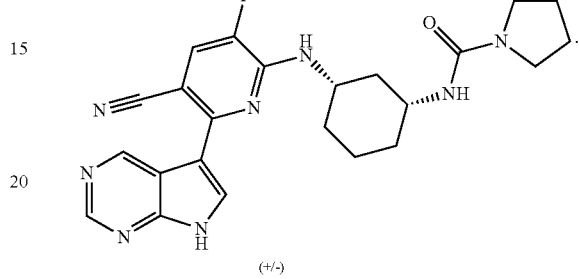

or a pharmaceutically acceptable salt of any of the foregoing.

18. A pharmaceutical composition comprising a compound of claim 17 and one or more pharmaceutically acceptable excipients.

19. A method of treating influenza in a subject in need thereof, comprising administering to said subject a therapeutically effective amount of at least one compound of claim 17.

* * * * *